United States Patent
Perez Zarate et al.

(10) Patent No.: US 10,796,018 B2
(45) Date of Patent: Oct. 6, 2020

(54) METHODS AND APPARATUS TO GENERATE AN OPTIMIZED WORKSCOPE

(71) Applicant: General Electric Company, Schenectady, NY (US)

(72) Inventors: Victor Manuel Perez Zarate, Niskayuna, NY (US); Luis Gabriel De Alba Rivera, Queretaro (MX); Brock Estel Osborn, Huntersville, NC (US); Katherine Tharp Nowicki, Cincinnati, OH (US); Michael William Bailey, Evendale, OH (US); Michael Evans Graham, Niskayuna, NY (US)

(73) Assignee: General Electric Company, Schenectadu, NY (US)

(*) Notice: Subject to any disclaimer, the term of this patent is extended or adjusted under 35 U.S.C. 154(b) by 385 days.

(21) Appl. No.: 15/809,804

(22) Filed: Nov. 10, 2017

(65) Prior Publication Data
US 2019/0146436 A1    May 16, 2019

(51) Int. Cl.
*G05B 19/042* (2006.01)
*G06Q 10/00* (2012.01)
(Continued)

(52) U.S. Cl.
CPC ........ *G06F 21/6245* (2013.01); *G06F 19/321* (2013.01); *G06F 19/3418* (2013.01);
(Continued)

(58) Field of Classification Search
CPC .............................. G05B 19/042; G06Q 10/20
(Continued)

(56) References Cited

U.S. PATENT DOCUMENTS

| | | | | |
|---|---|---|---|---|
| 6,067,486 A | * | 5/2000 | Aragones | B64F 5/60 701/29.6 |
| 6,732,040 B2 | * | 5/2004 | Sangeeta | G05B 23/0283 477/30 |

(Continued)

OTHER PUBLICATIONS

Pascual et al. (Optimal replacement and overhaul decisions with imperfect maintenance and warranty contracts, 2001, Reliability Engineering and System Safety 91 (2006) 241-248) (Year: 2006).*

(Continued)

*Primary Examiner* — Iftekhar A Khan
(74) *Attorney, Agent, or Firm* — Wood IP LLC

(57) ABSTRACT

Methods, apparatus, systems and articles of manufacture are disclosed to generate a workscope. An example apparatus includes a workscope mapper, workscope strategy analyzer, and workscope selector. The workscope strategy analyzer is to evaluate each of the plurality of workscopes using dynamic optimization to determine a maintenance value and benefit to an asset associated with each workscope based on a stage in a remaining life of a constraint at which the evaluation is executed and a state of the asset. The dynamic optimization is to determine a prediction of the maintenance value based on a probability of a future change in state and associated workscope value until the end of life of the constraint. The maintenance value, used to select a workscope from the plurality of workscopes, is to be determined by the dynamic optimization as a sum of the associated workscope values until the end of life of the constraint.

19 Claims, 18 Drawing Sheets

(51) Int. Cl.

| | |
|---|---|
| *G06F 21/62* | (2013.01) |
| *G06F 19/00* | (2018.01) |
| *G06Q 50/24* | (2012.01) |
| *H04N 1/00* | (2006.01) |
| *G06F 21/53* | (2013.01) |
| *G06F 21/60* | (2013.01) |
| *G06T 11/00* | (2006.01) |
| *G16H 40/67* | (2018.01) |
| *G16H 10/60* | (2018.01) |
| *G16H 30/20* | (2018.01) |

(52) U.S. Cl.
CPC ............ *G06F 21/53* (2013.01); *G06F 21/606* (2013.01); *G06Q 50/24* (2013.01); *G06T 11/00* (2013.01); *G16H 10/60* (2018.01); *G16H 30/20* (2018.01); *G16H 40/67* (2018.01); *H04N 1/00209* (2013.01); *H04N 1/00244* (2013.01); *G06F 2221/032* (2013.01); *G06F 2221/2149* (2013.01); *H04N 2201/0079* (2013.01)

(58) Field of Classification Search
USPC .......................................................... 703/7
See application file for complete search history.

(56) References Cited

U.S. PATENT DOCUMENTS

| | | | | | |
|---|---|---|---|---|---|
| 6,832,205 | B1* | 12/2004 | Aragones | ............... | G06Q 10/06 705/7.25 |
| 6,871,160 | B2* | 3/2005 | Jaw | ....................... | G01M 15/00 700/108 |
| 8,417,360 | B2* | 4/2013 | Sustaeta | ............... | G05B 13/024 700/28 |
| 8,560,376 | B2* | 10/2013 | Lienhardt | ............ | G06Q 10/0631 705/7.38 |
| 8,868,287 | B2* | 10/2014 | Delaye | ................ | G05B 23/0283 701/31.9 |
| 9,477,224 | B2* | 10/2016 | Khan | ................... | G05B 23/0283 |
| 10,417,614 | B2* | 9/2019 | Johnson | ............. | G05B 23/0251 |
| 2003/0040826 | A1* | 2/2003 | Hawman | .................. | G07C 3/00 700/116 |
| 2003/0167117 | A1* | 9/2003 | Sangeeta | .................. | G07C 3/00 701/100 |
| 2004/0138792 | A1* | 7/2004 | Foxford | ................. | G06Q 10/20 701/33.4 |
| 2006/0010152 | A1* | 1/2006 | Catalano | .................. | G06Q 10/06 |
| 2007/0156496 | A1* | 7/2007 | Avery | .................... | G06Q 10/087 705/305 |
| 2008/0162235 | A1* | 7/2008 | Tomastik | ......... | G06Q 10/06375 705/7.24 |
| 2008/0172268 | A1* | 7/2008 | Wingenter | ............. | G06Q 10/06 705/305 |
| 2008/0249828 | A1* | 10/2008 | MacAuley | ......... | G06Q 10/0631 705/7.13 |
| 2008/0300738 | A1* | 12/2008 | Coulmeau | ............... | G01C 21/20 701/3 |
| 2009/0048730 | A1* | 2/2009 | Akkaram | ............... | G07C 5/006 701/31.4 |
| 2009/0112569 | A1* | 4/2009 | Angus | ..................... | H04L 67/38 703/22 |
| 2010/0153080 | A1* | 6/2010 | Khan | .................. | G05B 23/0283 703/7 |
| 2010/0262442 | A1* | 10/2010 | Wingenter | ......... | G06Q 30/0283 705/7.38 |
| 2011/0054965 | A1* | 3/2011 | Katagiri | ............... | G06Q 10/063 705/7.11 |
| 2012/0166249 | A1* | 6/2012 | Jackson | ........... | G05B 19/41865 705/7.28 |
| 2012/0191496 | A1* | 7/2012 | Muench | ............. | G06Q 10/0631 705/7.13 |
| 2012/0221193 | A1* | 8/2012 | Delaye | ............... | G05B 23/0283 701/31.9 |
| 2012/0290104 | A1* | 11/2012 | Holt | ....................... | G06Q 10/00 700/29 |
| 2013/0110587 | A1* | 5/2013 | Nowicki | ................ | G06Q 10/06 705/7.37 |
| 2013/0179388 | A1* | 7/2013 | Agarwal | ................ | G06Q 10/06 706/47 |
| 2014/0052410 | A1* | 2/2014 | Tralshawala | .......... | F01D 21/003 702/183 |
| 2014/0278713 | A1* | 9/2014 | Zivelin | ............ | G06Q 10/06313 705/7.25 |
| 2015/0057783 | A1* | 2/2015 | Rossi | ..................... | G06Q 10/06 700/108 |
| 2016/0010628 | A1* | 1/2016 | Dhar | ....................... | F03D 17/00 702/34 |
| 2016/0125518 | A1* | 5/2016 | Doom | ....................... | B64F 5/00 705/39 |
| 2016/0231716 | A1* | 8/2016 | Johnson | ............... | G05B 13/041 |
| 2016/0247129 | A1* | 8/2016 | Song | ..................... | G06Q 10/20 |
| 2017/0192414 | A1* | 7/2017 | Mukkamala | ........... | G06Q 10/04 |
| 2017/0323240 | A1* | 11/2017 | Johnson | .......... | G06Q 10/06315 |
| 2017/0323274 | A1* | 11/2017 | Johnson | ............ | G06Q 10/0635 |
| 2017/0323403 | A1* | 11/2017 | Johnson | ............... | G06Q 10/087 |
| 2018/0164796 | A1* | 6/2018 | Garciamoreno | ........ | F01D 21/14 |
| 2019/0146470 | A1* | 5/2019 | Akkaram | ............ | G05B 23/0254 700/30 |
| 2019/0147411 | A1* | 5/2019 | John | ................ | G06Q 10/06315 705/305 |

OTHER PUBLICATIONS

Zhong et al. (Probability Evaluation Method of Gas Turbine Workscope Based on Survival Analysis, 2017, IEEE, pp. 1-5) (Year: 2017).*

Guo et al. ("Reliability Centered Preventive Maintenance Optimization for Aircraft Indicators", IEEE,2016, pp. 1-6) (Year: 2016).*

Euclides da Conceição Pereira Batalha ("Aircraft Engines Maintenance Costs and Reliability", Universidade Nova de Lisboa, pp. 1-72) (Year: 2012).*

Kang et al. ("An Approach to Maintenance Cost Estimation for Aircraft Engines", ASME, 2008, pp. 1-9) (Year: 2008).*

Donaldson et al, "Economic Impact of Derated Climb on Large Commercial Engines", 2007 Performance and Flight Operations Engineering Conference, 14 pages.

James et al., "Derated Climb Performance in Large Civil Aircraft", 2005 Performance and Flight Operations Engineering Conference, 14 Pages.

* cited by examiner

```
REQUIRE Set W of workscopes
• W = 0
• N = numStagesRemain
• minCost = initialCostEstimate
• WHILE{ 0 < N < M }
    ○   Cost = WorkScopeCost(WorkScope(W)) + ProbabilityIncurCost
    ○   IF{Cost is less than minCost}
        ▪   minCost = Cost
        ▪   currentBestWorkScope = WorkScope(W)
        ▪   W = W+1
        ▪   N = N-1
    ○   ENDIF
• ENDWHILE
• OUTPUT currentBestWorkScope
• OUTPUT minCost
```

FIG. 15

METHODS AND APPARATUS TO GENERATE AN OPTIMIZED WORKSCOPE

FIELD OF THE DISCLOSURE

This disclosure relates generally to engine workscope determination and, more particularly, to methods and apparatus to optimize or otherwise improve engine workscope.

BACKGROUND

In recent years, turbine engines have been increasingly utilized in a variety of applications and fields. Turbine engines are intricate machines with extensive availability, reliability, and serviceability requirements. Traditionally, maintaining turbine engines incur steep costs. Costs generally include having exceptionally skilled and trained maintenance personnel service the turbine engines. In some instances, costs are driven by replacing expensive components or by repairing complex sub-assemblies.

The pursuit of increasing turbine engine availability while reducing premature maintenance costs requires enhanced insight. Such insight is needed to determine when to perform typical maintenance tasks at generally appropriate service intervals. Traditionally, availability, reliability, and serviceability increase as enhanced insight is deployed.

The market for long-term contractual agreements has grown at high rates over recent years for many service organizations. As the service organizations establish long-term contractual agreements with their customers, it becomes important to understand the expected scope of work (also referred to as "workscope") including product, service, and/or other project result. In addition, the service organizations need to have an understanding of the planning of repairs (e.g., shop workload and/or workscope planning) and how the maintenance of components will affect management of their service contracts including time, cost, risk, etc.

BRIEF DESCRIPTION OF THE DRAWINGS

FIG. 15 illustrates example source code representative of example computer readable instructions that may be executed to implement the example asset workscope generation system of FIGS. 3-7 that may be used to implement the examples disclosed herein.

The figures are not to scale. Wherever possible, the same reference numbers will be used throughout the drawing(s) and accompanying written description to refer to the same or like parts.

BRIEF SUMMARY

Figure 1:
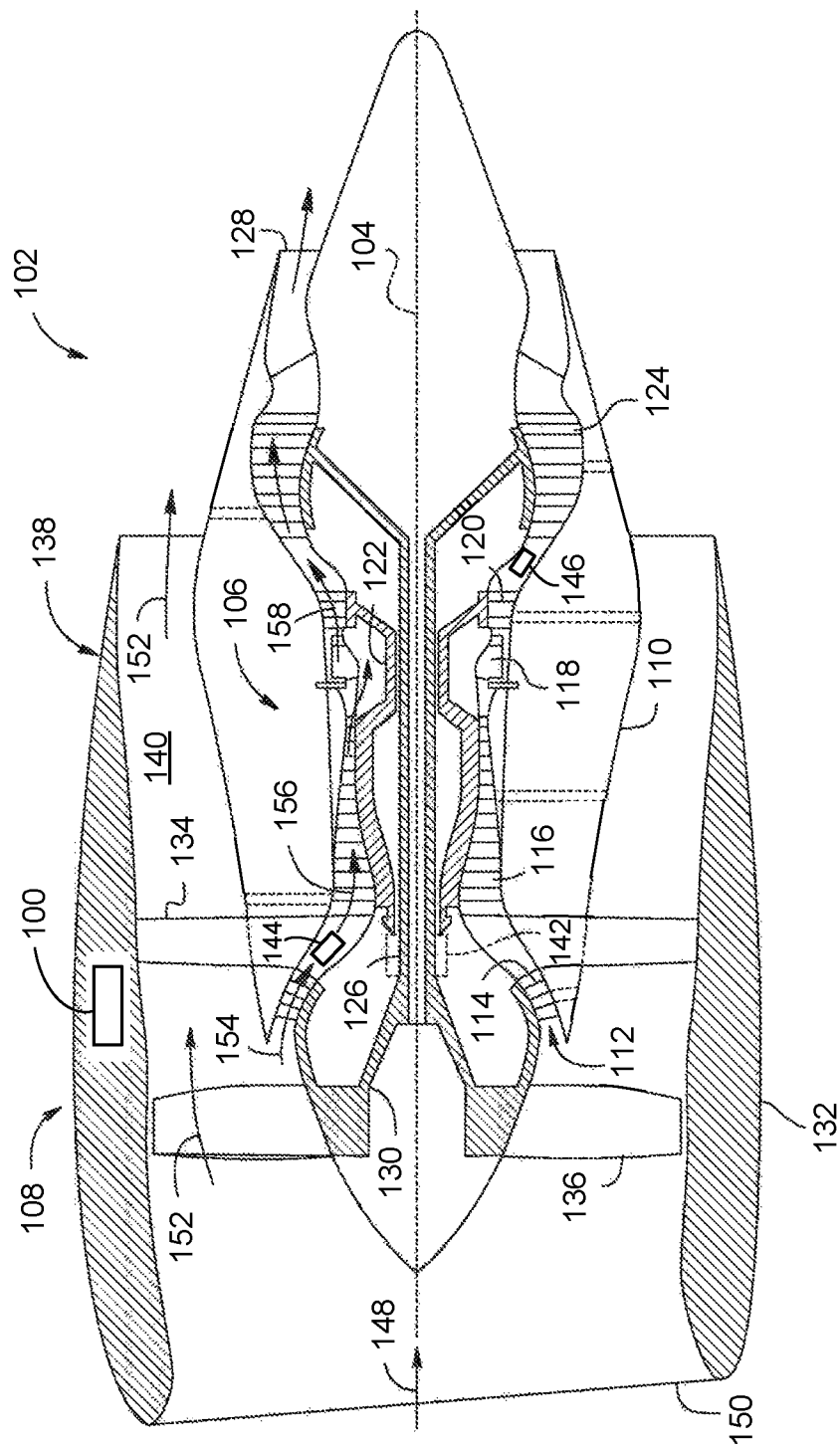
FIG. 1 illustrates an example gas turbine engine that can be utilized within an aircraft in which the examples disclosed herein can be implemented.

Methods, apparatus, systems, and articles of manufacture to determine and evaluate available workscopes to select an optimal, improved, and/or otherwise beneficial workscope from the available workscopes for a target asset are disclosed.

Certain examples provide an apparatus including a workscope mapper, a workscope strategy analyzer, and a workscope selector. The example workscope mapper is to process asset information and constraint information to generate a model of a target asset and a model of a constraint associated with the target asset. The example workscope mapper is to map shop visit drivers to a plurality of workscopes using the target asset model and the associated constraint model. Each of the example plurality of workscopes models maintenance of the target asset including tasks and resources associated with the maintenance of the target asset. The example workscope strategy analyzer is to evaluate each of the plurality of workscopes using dynamic optimization to determine a maintenance value to the target asset associated with each workscope based on a stage in a remaining life of the constraint at which the evaluation is executed and a state of the target asset. The example dynamic optimization is to determine a prediction of the maintenance value based on a probability of a future change in state and associated workscope value until the end of life of the constraint. The example maintenance value is to be determined by the dynamic optimization as a minimum sum of the associated workscope values until the end of life of the constraint. The example workscope selector is to select a workscope from the plurality of workscopes based on the evaluation of the plurality of workscopes by the workscope strategy analyzer including comparison of the maintenance value associated with each of the plurality of workscopes. The example workscope selector is to trigger maintenance with respect to the target asset according to the selected workscope.

Certain examples provide a non-transitory computer readable storage medium including instructions which when executed, cause a machine to implement at least a workscope mapper, a workscope strategy analyzer, and a workscope selector. The example workscope mapper is to process asset information and constraint information to generate a model of a target asset and a model of a constraint associated with the target asset. The example workscope mapper is to map shop visit drivers to a plurality of workscopes using the target asset model and the associated constraint model. Each of the example plurality of workscopes models maintenance of the target asset including tasks and resources associated with the maintenance of the target asset. The example workscope strategy analyzer is to evaluate each of the plurality of workscopes using dynamic optimization to determine a maintenance value to the target asset associated with each workscope based on a stage in a remaining life of the constraint at which the evaluation is executed and a state of the target asset. The example dynamic optimization is to determine a prediction of the maintenance value based on a probability of a future change in state and associated workscope value until the end of life of the constraint. The example maintenance value is to be determined by the dynamic optimization as a minimum sum of the associated workscope values until the end of life of the constraint. The example workscope selector is to select a workscope from the plurality of workscopes based on the evaluation of the plurality of workscopes by the workscope strategy analyzer including comparison of the maintenance value associated with each of the plurality of workscopes. The example workscope selector is to trigger maintenance with respect to the target asset according to the selected workscope.

Certain examples provide a computer-implemented method including processing, using a configured processor, asset information and constraint information to generate a model of a target asset and a model of a constraint associated with the target asset. The example method includes mapping, using the configured processor, shop visit drivers to a plurality of workscopes using the target asset model and the associated constraint model, each of the plurality of workscopes modeling maintenance of the target asset including tasks and resources associated with the maintenance of the target asset. The example method includes evaluating, using the configured processor, each of the plurality of workscopes using dynamic optimization to determine a maintenance value to the target asset associated with each workscope based on a stage in a remaining life of the constraint at which the evaluation is executed and a state of the target asset, the dynamic optimization to determine a prediction of the maintenance value based on a probability of a future change in state and associated workscope value until the end of life of the constraint, the maintenance value determined by the dynamic optimization as a minimum sum of the associated workscope values until the end of life of the constraint. The example method includes selecting, using the configured processor, a workscope from the plurality of workscopes based on the evaluation of the plurality of workscopes by the workscope strategy analyzer including comparison of the maintenance value associated with each of the plurality of workscopes. The example method includes triggering, based on the selected workscope and using the configured processor, maintenance with respect to the target asset according to the selected workscope.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized. The following detailed description is therefore, provided to describe an exemplary implementation and not to be taken limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module,", "engine,", "component," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, or system may include a hard-wires device that performs operations based on hard-wired logic of the device. Various modules, units, engines, and/or systems shown in the attached figures may represent the hardware that operates based on software or hardwired instructions, the software that directs hardware to perform the operations, or a combination thereof.

A turbine engine, also called a combustion turbine or a gas turbine, is a type of internal combustion engine. Turbine engines are commonly utilized in aircraft and power-generation applications. As used herein, the terms "asset," "aircraft turbine engine," "gas turbine," "land-based turbine engine," and "turbine engine" are used interchangeably. A basic operation of the turbine engine includes an intake of fresh atmospheric air flow through the front of the turbine engine with a fan. In some examples, the air flow travels through an intermediate-pressure compressor or a booster compressor located between the fan and a high-pressure compressor. The booster compressor is used to supercharge or boost the pressure of the air flow prior to the air flow entering the high-pressure compressor. The air flow can then travel through the high-pressure compressor that further pressurizes the air flow. The high-pressure compressor includes a group of blades attached to a shaft. The blades spin at high speed and subsequently compress the air flow. The high-pressure compressor then feeds the pressurized air flow to a combustion chamber. In some examples, the high-pressure compressor feeds the pressurized air flow at speeds of hundreds of miles per hour. In some instances, the combustion chamber includes one or more rings of fuel injectors that inject a steady stream of fuel into the combustion chamber, where the fuel mixes with the pressurized air flow.

In the combustion chamber of the turbine engine, the fuel is ignited with an electric spark provided by an igniter, where the fuel in some examples burns at temperatures of more than 2000 degrees Fahrenheit. The resulting combustion produces a high-temperature, high-pressure gas stream (e.g., hot combustion gas) that passes through another group of blades called a turbine. A turbine includes an intricate array of alternating rotating and stationary airfoil-section blades. As the hot combustion gas passes through the turbine, the hot combustion gas expands, causing the rotating blades to spin. The rotating blades serve at least two purposes. A first purpose of the rotating blades is to drive the booster compressor and/or the high-pressure compressor to draw more pressured air into the combustion chamber. For example, the turbine is attached to the same shaft as the high-pressure compressor in a direct-drive configuration, thus, the spinning of the turbine causes the high-pressure compressor to spin. A second purpose of the rotating blades is to spin a generator operatively coupled to the turbine section to produce electricity. For example, the turbine can generate electricity to be used by an aircraft, a power station, etc.

In the example of an aircraft turbine engine, after passing through the turbine, the hot combustion gas exits the aircraft turbine engine through a nozzle at the back of the aircraft turbine engine. As the hot combustion gas exits the nozzle, the aircraft turbine engine and the corresponding aircraft coupled to the aircraft turbine engine are accelerated forward (e.g., thrusted forward). In the example of a land-based turbine engine, after passing through the turbine, the hot combustion gas is dissipated, used to generate steam, etc.

A turbine engine (e.g., an aircraft turbine engine) typically includes components (e.g., asset components, etc.) or modules (e.g., asset modules or assemblies including one or more components, etc.) for operation such as a fan (e.g., a fan section), a booster compressor, a high-pressure compressor, a high-pressure turbine, and a low-pressure turbine. The components can degrade over time due to demanding operating conditions such as extreme temperature and vibration. In some instances, debris or other objects enter the turbine engine via the fan and cause damage to one or more components. Routine maintenance intervals and service checks can be implemented to inspect for degradation and/or damage. However, in some instances, taking the turbine engine offline or off wing to perform maintenance includes taking an entire system, such as an aircraft, offline. In addition to prematurely replacing expensive components, aircraft non-operation can incur additional costs such as lost revenue, labor costs, etc. Monitoring components for degradation can provide actionable information for maintenance personnel to replace a component of the turbine engine when necessary, to optimally schedule maintenance tasks of the turbine engine based on contractual and/or maintenance resources, etc. While example assets described herein have been illustrated in terms of engines, such as a turbine engine, diesel engine, etc., the systems and methods disclosed and described herein can also apply to assets such as wind turbines, additive printing machines, computed tomography scanners, etc.

Examples disclosed herein include an example asset workscope generation system (AWGS) to combine field data, statistical analytic tools, engineering physics-based models, prediction simulators integrated with forecasted mission requirements, etc., to develop a recommended modular workscope and a timing to perform the recommended modular workscope for an asset such as a turbine engine to satisfy customer and field personnel expectations. As used herein, the term "workscope" (also referred to as a "scope of work") refers to a set of tasks (e.g., one or more maintenance tasks, service tasks, etc.) executed by maintenance personnel to improve an operating condition of an asset, where the operating condition is determined based on requirements such as contractual requirements, environmental requirements, regulatory requirements, utilization requirements, etc., and/or a combination thereof. The workscope can include a strategy or a plan for performing one or more maintenance activities upon components of a system.

A workscope may include, without limitation, a list of components within the system, one or more dates and/or times that a component should be repaired or have maintenance performed on it, an expected cost of completing each step or maintenance activity of the workscope, and/or one or more probabilities of each component failing or requiring a maintenance activity to be performed during a time period of the workscope. Alternatively or additionally, a workscope may include an amount of use and/or a number cycles (e.g., in the case of a component of a rotating machine) that the component has experienced (hereinafter referred to as a "cycle time" of the component), a cost to repair the component, and/or a cost to replace the component.

In certain examples, a workscope is determined based on multiple inputs including cumulative damage models of parts, modules, and systems, statistical models (e.g., parametric (e.g., Weibull probability distribution, etc.) and/or non-parametric models), financial models, contract term, conditions, customer expectations, etc. One or more models can be implemented using a digital twin (e.g., via an artificial neural network and/or other machine learning implementation of an aspect and/or characteristic of the physical asset, etc.), for example. Certain examples allow the workscope model inputs to evaluate the financial impact of a series of possible workscopes over the life of a service contract. A user can then create an optimized and/or otherwise improved workscope selection with associated predicted outcomes.

In some examples, the AWGS obtains asset monitoring information from one or more assets, a network, a server, etc. As used herein, the term asset monitoring information refers to information corresponding to one or more assets such as asset sensor information, asset environmental information, asset utilization information, asset configuration information, asset history information, asset class history information, asset workscope quantifiers, etc.

In some examples, the AWGS identifies target assets for removal from service (e.g., removal from an aircraft, removal from a facility, removal from use, etc.) based on calculating an asset health quantifier. As used herein, the term "asset health quantifier" refers to a numerical representation corresponding to a health status, an operational status, etc., of an asset, an asset component, etc. For example, the asset health quantifier can be represented by a percentage of useful life remaining, a number of flight cycles (e.g., a number of flight cycles to be executed before service is performed, etc.), a quantity of time-on-wing (TOW) hours (e.g., a number of time-on-wing hours before service is performed, etc.), etc. For example, an asset health quantifier of 75% for a turbine engine booster compressor can correspond to the booster compressor having 75% of useful life remaining before the booster compressor may become non-responsive or requires a maintenance action. In another example, an asset health quantifier of 500 cycles for a turbine engine fan section can correspond to the turbine engine fan section executing 500 cycles before the fan section can be serviced to satisfy a contractual requirement.

In some examples, the AWGS can execute one or more engineering physics-based models, historical information-based models, statistical models, etc., and/or a combination thereof to generate an actual asset health quantifier for an asset, an asset component, an asset module, etc. In some examples, the AWGS can generate a projected asset health quantifier based on forecasted mission requirements of the asset (e.g., forecasted contractual requirements, forecasted environmental information, etc.).

In some examples, the AWGS can identify one or more target assets for removal based on comparing one or more asset health quantifiers (e.g., an actual asset health quantifier, a projected asset health quantifier, etc.) to a threshold, determine whether the one or more asset health quantifiers satisfy the threshold, and identify the one or more target assets for removal based on the comparison.

In some examples, the AWGS generates a workscope task for the target asset. For example, the AWGS can identify a set of tasks (e.g., maintenance tasks, service tasks, etc.) to perform maintenance on a fan section (e.g., one or more fan blades, etc.) of a turbine engine. For example, the AWGS can identify maintenance costs corresponding to each task in the set of tasks. For example, the AWGS can calculate a cost based on a quantity of maintenance personnel and corresponding man-hours to perform a maintenance task, a quantity of components (e.g., a quantity of replacement parts, spare parts, shop-supplied parts, etc., and/or a combination thereof) to perform the maintenance task, a monetary cost for each of the components, etc.

In some examples, the AWGS optimizes and/or otherwise improves a workscope based on the generated workscope tasks for the target asset. For example, the AWGS can generate a plurality of workscopes in which each workscope includes a combination of one or more of the generated workscope tasks. The example AWGS can calculate an estimate asset health quantifier for the target asset based on estimating what the asset health quantifier for the target asset can be in response to performing a specified workscope on the target asset. The example AWGS can calculate an estimate asset health quantifier for each one of the generated workscopes. The example AWGS can identify a workscope for the target asset based on one or more factors such as comparing the calculated estimate asset health quantifiers to contractual requirements, customer requirements, operational constraints, etc., and/or a combination thereof.

In some examples, the AWGS calculates a workscope quantifier based on comparing a first asset health quantifier for a target asset to a second asset health quantifier for the target asset. For example, the first asset health quantifier can be an asset health quantifier (e.g., an actual asset health quantifier, a projected asset health quantifier, etc.) of the target asset prior to completing a workscope on the target asset. The second asset health quantifier can be an asset health quantifier (e.g., an actual asset health quantifier, a projected asset health quantifier, etc.) of the target asset after completing the workscope on the target asset. For example, the AWGS can calculate a workscope quantifier by calculating a difference between the first and the second asset health quantifiers.

In some examples, the AWGS can compare the workscope quantifier to a workscope quantifier threshold and determine whether the workscope quantifier threshold has been satisfied based on the comparison. In some examples, the AWGS can modify one or more components of the AWGS in response to the workscope quantifier threshold being satisfied. For example, the AWGS can update one or more models, one or more parameters corresponding to a maintenance task, improve an optimization parameter for evaluating generated workscopes, etc., and/or a combination thereof in response to the workscope quantifier threshold being satisfied. While example assets described herein have been illustrated in terms of engines, such as a turbine engine, diesel engine, etc., the systems and methods disclosed and described herein can also apply to assets such as wind turbines, additive printing machines, locomotive engines, health imaging equipment such as computed tomography scanners, etc., or any other type of mechanical, electrical, or electro-mechanical device. Additionally or alternatively, the systems and methods disclosed and described herein can also apply to any asset that has modular elements that require maintenance planning and scheduling a removal within requirement constraints such as contractual constraints corresponding to a management of spare assets.

Examples disclosed herein include an asset health calculator apparatus to identify a target asset for removal from service based on calculating an asset health quantifier of the target asset. In some examples, the asset health calculator apparatus obtains asset monitoring information corresponding to the target asset. For example, the asset health calculator apparatus can obtain asset sensor information, asset environmental information, asset utilization information, etc., and/or a combination thereof corresponding to the target asset.

In some examples, the asset health calculator apparatus executes one or more models such as an engineering physics-based model, a statistical model, etc., to generate an asset health quantifier for an asset, an asset component, an asset module, etc. In some examples, the asset health calculator apparatus generates a projected asset health quantifier based on forecasted mission requirements of the asset such as forecasted environmental information, forecasted utilization information, etc., to determine whether a degradation of the asset component will cause an unexpected shop visit (e.g., a shop visit prior to a next scheduled or anticipated shop visit, etc.)

In some examples, the asset health calculator apparatus calculates a projected asset health quantifier of an asset component by predicting an estimate of the actual asset health quantifier of the asset component based on an anticipated deterioration of the asset component over time. For example, the asset health calculator apparatus can predict the deterioration by using the actual asset health quantifier as an initial actual asset health quantifier of the asset component, and extrapolating the initial actual asset health quantifier to the projected asset health quantifier by executing one or more models using forecasted mission requirements including a number of flight cycles, a quantity of time-on-wing hours, etc.

In some examples, the asset health calculator apparatus aggregates and ranks the actual asset health quantifiers, the projected asset health quantifiers, etc. For example, the asset health calculator apparatus can rank assets or components of the assets based on the generated asset health quantifiers. In some examples, the asset health calculator apparatus compares an asset health quantifier to a threshold (e.g., an asset health quantifier threshold, a maintenance quantifier threshold, etc.) and determines whether the asset health quantifier satisfies the threshold based on the comparison.

In some examples, the asset health calculator apparatus identifies a first set of candidate assets including one or more assets as candidate(s) for removal based on comparing an asset health quantifier of an asset to a threshold and determining whether the asset health quantifier satisfies the threshold based on the comparison. For example, the asset health calculator apparatus can identify a turbine engine for removal from service to perform a maintenance activity on the turbine engine based on an asset health quantifier for the turbine engine satisfying a threshold.

In some examples, the asset health calculator apparatus identifies a second set of candidate assets including one or more assets as candidate(s) for removal based on non-asset monitoring information. For example, the asset health calculator apparatus can identify a turbine engine for removal based on a time interval between maintenance tasks specified in a contract, customer technical forecast information, customer spare part information, etc., for the turbine engine. As used herein, the term "contract" refers to an agreement between a turbine engine operator (e.g., an airline, a manufacturing plant, a power plant, etc.) and a turbine engine maintenance provider in which the turbine engine maintenance provider performs maintenance, service, etc., on an asset owned by the turbine engine operator.

In some examples, the asset health calculator apparatus compares candidate assets in the first set to the second set. In some examples, the asset health calculator apparatus identifies target assets for removal based on the comparison. In some examples, the asset health calculator apparatus generates a removal schedule for the identified target assets. For example, the asset health calculator apparatus can determine that the identified target assets correspond to one contract or more than one contract. For example, in response to determining that the target assets correspond to one contract, the asset health calculator apparatus can generate an optimal removal schedule of the target assets based on performing an optimization process such as an iterated local search.

In another example, in response to determining that the target assets correspond to more than one contract, the asset health calculator apparatus can generate a removal schedule for the target assets using methods such as integer programming, myopic optimization (e.g., a rolling optimization method, etc.), single level optimization, top-down optimization, bottom-up optimization, etc., and/or a combination thereof. For example, the asset health calculator apparatus can generate a removal schedule using single level optimization by optimizing and/or otherwise improving each asset corresponding to each contract simultaneously (or substantially simultaneously given data processing, transmission, and storage latency).

In another example, the asset health calculator apparatus can generate a removal schedule using top-down optimization by generating a high-level, top-level, etc., target removal schedule for each contract, generating a candidate removal schedule for each contract, and generating an optimized and/or otherwise improved removal schedule for the contracts based on the comparison of the target removal schedules to the candidate removal schedules. In another example, the asset health calculator apparatus can generate a removal schedule using bottom-up optimization by generating candidate removal schedules for each contract, combining the candidate removal schedules, and re-adjusting the candidate removal schedules to help ensure global feasibility with respect to one or more factors such as customer constraints, maintenance facility constraints, spare part availability constraints, etc., and/or a combination thereof.

In certain examples, the AWGS includes a Workscope Strategy Analyzer (WSA) that evaluates, for each possible workscope strategy, a financial, availability (e.g., uptime vs. downtime), resource, and/or other impact of a series of possible workscopes over the life of a service contract. The WSA facilitates creation of an optimized and/or otherwise improved workscope selection with associated predicted outcomes. For example, a workscope selection can be generated by obtaining specific contract information and mapping failure mode distributions to workscope models to construct a workscope model with associated price, cost and billing structure. For a given shop visit, probabilities associated with failure modes for workscope options can be determined using a dynamic programming approach which is propagated to the end of the contract.

In certain examples, for each analytical tool available that can trigger work on a part or module, the analytical tool can be mapped to a minimum workscope and multiple analytical tools can be combined to define a minimum workscope. Then, uncertainty cam be propagated for each analytic and combine at the part/module and engine level. The combined uncertainty feeds an algorithm to perform analytical trade-offs related to a cost of overhauling and benefits to financial and time-on-wing terms.

In certain examples, a prediction tool generates or identifies one or more workscopes from which a workscope that meets a predefined criterion or criteria can be selected. The prediction tool receives inputs from other tools, from the user, and/or from another system or device. In an example, the prediction tool receives engine information from an analyzer tool and receives workscope financial information from a financial model tool. More specifically, in an example, the engine information received from the analyzer tool includes, without limitation, an amount of time that engine has been in use since a most recent maintenance event, an amount of time that one or more engine components have been in use since the most recent maintenance or repair event, one or more components that have failed, and/or any other data that enables the prediction tool. The workscope financial information received from the financial model tool includes a financial impact of each maintenance activity defined within each workscope, such as a financial impact of maintenance or repair of each component at one or more future dates. In an example, the financial impact includes a cost of performing maintenance activities on the components. However, the financial impact additionally or alternatively includes a price, a profit, and/or any other financial effect associated with performing maintenance activities on the components. Alternatively or additionally, the prediction tool may receive other inputs, such as an engine condition, diagnostics data, workscope requirements, and/or any other input.

As used herein, the term "maintenance event" refers to an event in which the system (e.g., the engine) or components thereof are taken to a maintenance or repair facility, or "shop," to perform one or more maintenance activities on the system or components. Maintenance events are also known as "shop visits." These maintenance events may include failure driven events, where the system or component is taken to the facility as a result of a failure, and may also include non-failure driven visits, such as visits to the facility for preventative maintenance. As used herein, the term "maintenance activity" refers to performing maintenance on a system or component, and/or repairing the system or component.

In an example, the prediction tool generates an output indicative of one or more workscopes that are available to be performed on the engine (hereinafter referred to as "available workscopes"). In one embodiment, each workscope defines a different set of maintenance activities to be performed on the components than each other workscope. In an example, the prediction tool identifies or generates a "base" workscope, a "full" workscope, and/or one or more alternative workscopes that are available to be performed on the engine. In an example, the base workscope is a minimal set of maintenance activities to be performed on the engine and/or engine components. Alternatively, the base workscope may be a predetermined or "default" set of repair and/or maintenance activities to be performed on the engine and/or engine components. For example, the base workscope may include only repairing components that have failed and/or that are identified as "life-limited" components. As used herein, the term "life-limited" refers to a component that is required to be replaced and/or repaired within a predetermined time period. The alternative workscopes include additional, and/or different, repair and/or maintenance activities that may be performed on the engine and/or engine components as compared to the activities identified in the base workscope. The full workscope is a full set of maintenance activities to be performed on each component of the system. For example, the full workscope may include performing a maintenance activity on each component of the system when the system and/or components are taken to the maintenance facility, even if the components are not identified as requiring maintenance or repair. The available workscopes (e.g., the base workscope, the full workscope, and/or the alternative workscopes) are transmitted to the financial model tool and/or to analyzer tool.

In an example, the financial model tool receives inputs from the prediction tool and analyzer tool. The financial model tool generates outputs indicative of financial information (e.g., the financial impact) associated with each workscope and transmits the outputs to the prediction tool and the analyzer tool. The financial information includes, for example, a cost of each maintenance activity of each workscope and/or any other financial impact of each maintenance activity. In an example, the financial model tool receives a list of available workscopes from the prediction tool and/or from the analyzer tool. In an example, the financial model tool also receives data regarding a service contract or another instrument identifying repair and/or maintenance obligations for the engine and/or engine components, and a time period in which the service contract is in force. In an example, the financial model tool calculates the cost and/or price (or other financial impact) of each maintenance activity of each workscope by calculating the repair and/or maintenance costs and/or prices, for example, associated with each activity identified in each workscope. In an example, the financial model tool generates quotations for approval for one or more workscopes for a given set of requirements and generates a cost and price for the workscopes based on historical records and/or business plans. The financial model tool transmits the determined cost and/or price, or other financial impact, of each available workscope (e.g., the cost of the maintenance activities of the base workscope, the full workscope, and/or of each alternative workscope) to the prediction tool and/or to the analyzer tool.

In an example, the analyzer too receives inputs from the prediction tool and the financial model tool. Moreover, the analyzer tool generates outputs and transmits the outputs to the prediction tool and the financial model tool. The analyzer tool receives the list of available workscopes and the financial information from the prediction tool and/or from the financial model tool. The analyzer tool selects and/or presents to the user a recommended workscope based on the inputs received. For example, the analyzer tool calculates a probability distribution of expected maintenance activities within each workscope and selects a workscope with the lowest expected cost and/or price. Alternatively, the analyzer tool selects a workscope that satisfies any other criterion or criteria identified by the user or by a system or device. For example, the analyzer tool determines an expected effect of each workscope and selects the workscope that has the expected effect that best satisfies the criterion or criteria. The expected effect may include, for example, one or more of an expected cost, an expected price, an expected profit, an expected cash flow, an expected maintenance facility loading, an expected spare engine capacity or availability, and/or an expected "time on wing" interval of the workscope. Accordingly, in the example, the analyzer tool may select a workscope that has a lowest expected cost for the maintenance activities expected to be performed during a predefined time interval. However, it should be recognized that analyzer tool may select a workscope in which the expected effect of the workscope satisfies any other criterion or criteria during the time interval.

In an example, the analyzer tool quantifies the benefits and costs of the workscopes received by, for example, calculating the probability (e.g., a Weibull distribution, etc.) of each workscope's "time on wing" (TOW) (e.g., each workscope's effect on the engine's time in operation) and financial output (e.g., an effect of each workscope on an amount of revenue expected to be generated by the engine as a result of each workscope). In an example, for each available workscope, the analyzer tool presents to the user a series of probability distributions representing expected financial and operational future outcomes of performing the workscopes on the engine and/or engine components throughout a plurality of future repair and/or maintenance events.

In the example, the analyzer tool receives inputs (hereinafter referred to as "external inputs") from an external source such as from a user or from a remote device or system. The external inputs include one or more of an engine condition, a condition of one or more engine components, an amount of time or engine cycles in which the engine and/or engine components have been in operation, an indication of a failing or failed engine component, a set or list of business constraints and/or constraints due to one or more service or other contracts, an amount of time that one or more service or other contracts are in force, a notification or an indication that one or more components are or include life-limited parts, and/or failure distributions computed from historical field data. Alternatively, any of the external inputs may be received by other tools and may be transmitted to the analyzer tool.

In an example, the analyzer tool uses a state-based solution or model to provide a logistical framework for selecting among workscope alternatives (e.g., to facilitate selecting an optimal or recommended workscope from the list of available workscopes). In an example, the analyzer tool determines which workscope should be performed at each failure driven shop visit in order to minimize the total expected cost (e.g., of maintenance activities within a service contract) over a specified time interval (e.g., during the remaining time that the service contract is in effect). The analyzer tool determines the lowest expected maintenance cost (or determines an expected effect that satisfies any other criterion or criteria) for the system associated with the service contract using a dynamic programming solution, for example.

Asset maintenance management involves a detailed knowledge of the durability of the parts, modules and interactions due to assembly of the asset plus. As more analytic models are available that track the durability of components and modules, along with complexities in how different maintenance contracts are engineered, it becomes very complex to evaluate the financial implications of different workscoping decisions. Certain examples combine available technical, analytical and financial information to compute the financial implications for different workscoping scenarios.

FIG. 1 is a schematic illustration of an example turbine engine controller 100 monitoring an example gas turbine engine 102. In the illustrated example, the turbine engine controller 100 is a full-authority digital engine control (FADEC) unit. For example, the turbine engine controller 100 can include a closed loop control module to generate a control input (e.g., a thrust command, a de-rate parameter, etc.) to the engine 102 based on an engine input (e.g., a pilot command, an aircraft control system command, etc.). Alternatively, the turbine engine controller 100 may be any other type of data acquisition and/or control computing device. FIG. 1 illustrates a cross-sectional view of the engine 102 that can be utilized within an aircraft in accordance with aspects of the disclosed examples. The gas turbine engine 102 is shown having a longitudinal or axial centerline axis 104 extending throughout the gas turbine engine 102 for reference purposes. In general, the engine 102 can include a core gas turbine engine 106 and a fan section 108 positioned upstream thereof. The core gas turbine engine 106 can generally include a substantially tubular outer casing 110 that defines an annular inlet 112. In addition, the outer casing 110 can further enclose and support a booster compressor 114 for increasing the pressure of the air that enters the core gas turbine engine 106 to a first pressure level. A high-pressure, multi-stage, axial-flow compressor 116 can then receive the pressurized air from the booster compressor 114 and further increase the pressure of such air to a second pressure level. Alternatively, the high-pressure, multi-stage compressor 116 can be a high-pressure, multi-stage centrifugal compressor or a high-pressure, multi-stage axial-centrifugal compressor.

In the illustrated example of FIG. 1, the pressurized air exiting the high-pressure compressor 116 can then flow to a combustor 118 within which fuel is injected into the flow of pressurized air, with the resulting mixture being combusted within the combustor 118. The high-energy combustion products are directed from the combustor 118 along the hot gas path of the engine 102 to a first (high-pressure) turbine 120 for driving the high-pressure compressor 116 via a first (high-pressure) drive shaft 122, and then to a second (low-pressure) turbine 124 for driving the booster compressor 114 and fan section 108 via a second (low-pressure) drive shaft 126 that is generally coaxial with first drive shaft 122. After driving each of the turbines 120 and 124, the combustion products can be expelled from the core gas turbine engine 106 via an exhaust nozzle 128 to provide propulsive jet thrust.

In some examples, each of the compressors 114, 116 can include a plurality of compressor stages, with each stage including both an annular array of stationary compressor vanes and an annular array of rotating compressor blades positioned immediately downstream of the compressor vanes. Similarly, each of the turbines 120, 124 can include a plurality of turbine stages, with each stage including both an annular array of stationary nozzle vanes and an annular array of rotating turbine blades positioned immediately downstream of the nozzle vanes.

Additionally, as shown in FIG. 1, the fan section 108 of the engine 102 can generally include a rotatable, axial-flow fan rotor assembly 130 that is configured to be surrounded by an annular fan casing 132. The fan casing 132 can be configured to be supported relative to the core gas turbine engine 106 by a plurality of substantially radially-extending, circumferentially-spaced outlet guide vanes 134. As such, the fan casing 132 can enclose the fan rotor assembly 130 and its corresponding fan rotor blades 136. Moreover, a downstream section 138 of the fan casing 132 can extend over an outer portion of the core gas turbine engine 106 to define a secondary, or by-pass, airflow conduit 140 that provides additional propulsive jet thrust.

In some examples, the second (low-pressure) drive shaft 126 is directly coupled to the fan rotor assembly 130 to provide a direct-drive configuration. Alternatively, the second drive shaft 126 can be coupled to the fan rotor assembly 130 via a speed reduction device 142 (e.g., a reduction gear or gearbox) to provide an indirect-drive or geared drive configuration. Such a speed reduction device(s) can also be provided between any other suitable shafts and/or spools within the engine 102 as desired or required.

In the illustrated example of FIG. 1, the engine 102 includes sensors 144, 146 communicatively coupled to the turbine engine controller 100. Alternatively, the sensors 144, 146 can be communicatively coupled to a control system of an aircraft coupled to the engine 102, in which the control system is communicatively coupled to the example turbine engine controller 100. In the illustrated example, the sensors 144, 146 are gas-path temperature sensors (e.g., exhaust gas-path temperature sensors, etc.). For example, the sensors 144, 146 can be monitoring a compressor inlet temperature and a temperature of gas exiting the high-pressure turbine 120. Alternatively, the sensors 144, 146 can be chip detector sensors (e.g., magnetic chip detector sensors, etc.), dust sensors, flow sensors, gas-path pressure sensors, rotor speed sensors, vibration sensors, position sensors (e.g., actuator position sensors, sensors detailing variable geometry, etc.), etc. Although the sensors 144, 146 are depicted in FIG. 1 as being at specific locations, the sensors 144, 146 can be located elsewhere on the engine 102. Additionally or alternatively, there can be more than two sensors 144, 146 located on the engine 102. A typical implementation has six gas-path temperature sensors 144, 146. Additionally or alternatively, there can be more than one example turbine engine controller 100 coupled to the engine 102. Although the example turbine engine controller 100 is depicted in FIG. 1 as being proximate the fan section 108, the turbine engine controller 100 can be located elsewhere on the engine 102 or elsewhere on the aircraft coupled to the engine 102.

During operation of the engine 102, an initial air flow (indicated by arrow 148) can enter the engine 102 through an associated inlet 150 of the fan casing 132. The air flow 148 then passes through the fan blades 136 and splits into a first compressed air flow (indicated by arrow 152) that moves through conduit 140 and a second compressed air flow (indicated by arrow 154) which enters the booster compressor 114. The pressure of the second compressed air flow 154 is then increased and enters the high-pressure compressor 116 (as indicated by arrow 156). After mixing with fuel and being combusted within the combustor 118, the combustion products 158 exit the combustor 118 and flow through the first turbine 120. Thereafter, the combustion products 158 flow through the second turbine 124 and exit the exhaust nozzle 128 to provide thrust for the engine 102.

Figure 2:
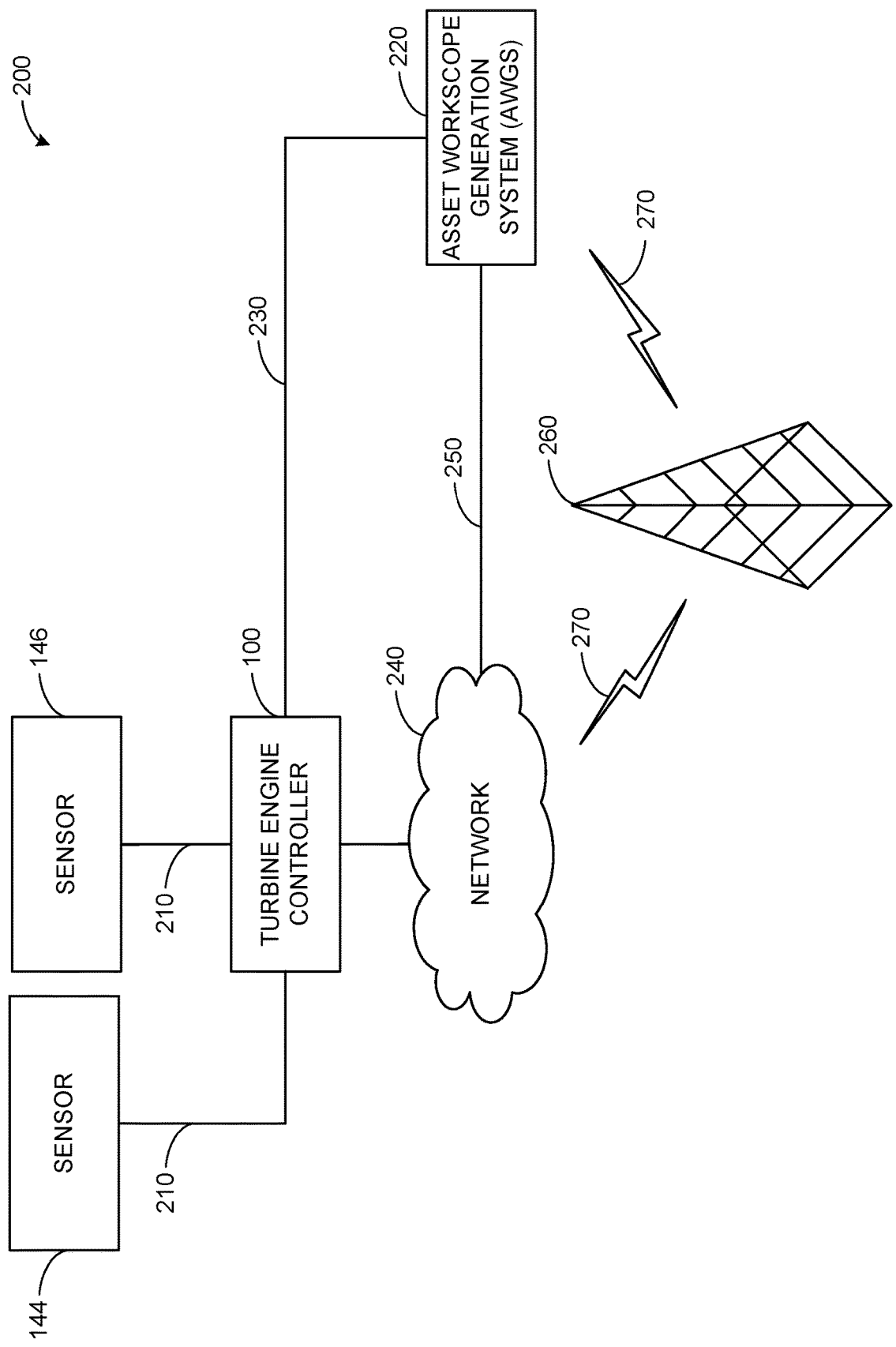
FIG. 2 is a block diagram of an example environment in which an example asset workscope generation system monitors the example gas turbine engine of FIG. 1.

FIG. 2 is a schematic illustration of an example asset monitoring system 200 for the gas turbine engine 102 of FIG. 1. In the illustrated example of FIG. 2, the sensors 144, 146 of FIG. 1 are communicatively coupled to the turbine engine controller 100 via sensor connections 210. The example turbine engine controller 100 obtains asset sensor information (e.g., a pressure, a temperature, a speed of a rotor, etc.) from the sensors 144, 146 to monitor an operation of the gas turbine engine 102. The sensor connections 210 can include direct wired or direct wireless connections. For example, a direct wired connection can involve a direct connection using wires in a harness connecting the sensors to the turbine engine controller 100, or a bus such as the Engine Area Distributed Interconnect Network (EADIN) bus. In another example, the direct wireless connections can implement a Bluetooth® connection, a Wi-Fi Direct® connection, or any other wireless communication protocol. Further shown in FIG. 2 are an example asset workscope generation system (AWGS) 220, an example AWGS direct connection 230, an example network 240, an example AWGS network connection 250, an example wireless communication system 260, and an example wireless communication links 270. As described further below, the example AWGS 220 can include a workscope strategy analyzer (WSA) to evaluate potential workscope strategies to determine an improved or "optimized" workscope for an asset.

In the illustrated example of FIG. 2, the example turbine engine controller 100 is shown to be communicatively coupled to the AWGS 220 via the AWGS direct connection 230. For example, the AWGS 220 can obtain asset operation information such as flight data (e.g., altitudes, turbine engine speeds, engine exhaust temperatures, etc.), asset sensor information, etc., from the turbine engine controller 100 via the AWGS direct connection 230. The example AWGS direct connection 230 can be a direct wired or a direct wireless connection. For example, the AWGS 220 can download asset information (e.g., asset operation information, asset sensor information, etc.) of the engine 102 via a manual download of the data from the turbine engine controller 100 to a computing device such as a laptop, a server, etc., followed by a subsequent upload to the AWGS 220. Alternatively, the example AWGS 220 can be directly connected to the turbine engine controller 100 to obtain asset information.

The AWGS 220 of the illustrated example is a server that collects and processes asset information of the engine 102. Alternatively or in addition, the example AWGS 220 can be a laptop, a desktop computer, a tablet, or any type of computing device or a network including any number of computing devices. The example AWGS 220 analyzes the asset information of the engine 102 to determine an asset workscope. For example, the AWGS 220 can determine that the high-pressure compressor 116 of FIG. 1 requires a water-wash based on a comparison of an asset health quantifier of the high-pressure compressor 116 to an asset health quantifier threshold corresponding to the high-pressure compressor 116, an elapsing of a time interval specified in a contract, etc.

Additionally or alternatively, the example AWGS 220 can obtain asset information from the example turbine engine controller 100 via the network 240. For example, the AWGS 220 can obtain asset information of the engine 102 from the turbine engine controller 100 by connecting to the network 240 via the AWGS network connection 250. The example AWGS network connection 250 can be a direct wired or a direct wireless connection. For example, the turbine engine controller 100 can transmit asset information to a control system of an aircraft coupled to the engine 102. The aircraft control system can subsequently transmit the asset information to the example AWGS 220 via the network 240 (e.g., via the AWGS network connection 250, the wireless communication links 270, etc.).

The example network 240 of the illustrated example of FIG. 2 is the Internet. However, the example network 240 can be implemented using any suitable wired and/or wireless network(s) including, for example, one or more data buses, one or more Local Area Networks (LANs), one or more wireless LANs, one or more cellular networks, one or more private networks, one or more public networks, etc. The example network 240 enables the example turbine engine controller 100 to be in communication with the example AWGS 220. As used herein, the phrase "in communication," including variances therefore, encompasses direct communication and/or indirect communication through one or more intermediary components and does not require direct physical (e.g., wired) communication and/or constant communication, but rather includes selective communication at periodic and/or aperiodic intervals, as well as one-time events.

In some examples, the turbine engine controller 100 is unable to transmit asset information to the AWGS 220 via the AWGS direct connection 230, the AWGS network connection 250, etc. For example, a routing device upstream of the AWGS 220 can stop providing functional routing capabilities to the AWGS 220. In the illustrated example, the turbine engine health monitoring system 200 includes additional capabilities to enable communication (e.g., data transfer) between the AWGS 220 and the network 240. As shown in FIG. 2, the example AWGS 220 and the example network 240 include the capabilities to transmit and/or receive asset information through the example wireless communication system 260 (e.g., the cellular communication system, the satellite communication system, the air band radio communication system, the Aircraft Communications Addressing and Reporting System (ACARS), etc.) via the example wireless communication links 270.

The wireless communication links 270 of the illustrated example of FIG. 2 are cellular communication links. However, any other method and/or system of communication can additionally or alternatively be used such as an Ethernet connection, a Bluetooth connection, a Wi-Fi connection, a satellite connection, etc. Further, the example wireless communication links 270 of FIG. 2 can implement cellular connections via a Global System for Mobile Communications (GSM). However, any other systems and/or protocols for communications can be used such as Time Division Multiple Access (TDMA), Code Division Multiple Access (CDMA), Worldwide Interoperability for Microwave Access (WiMAX), Long Term Evolution (LTE), etc.

Figure 3:
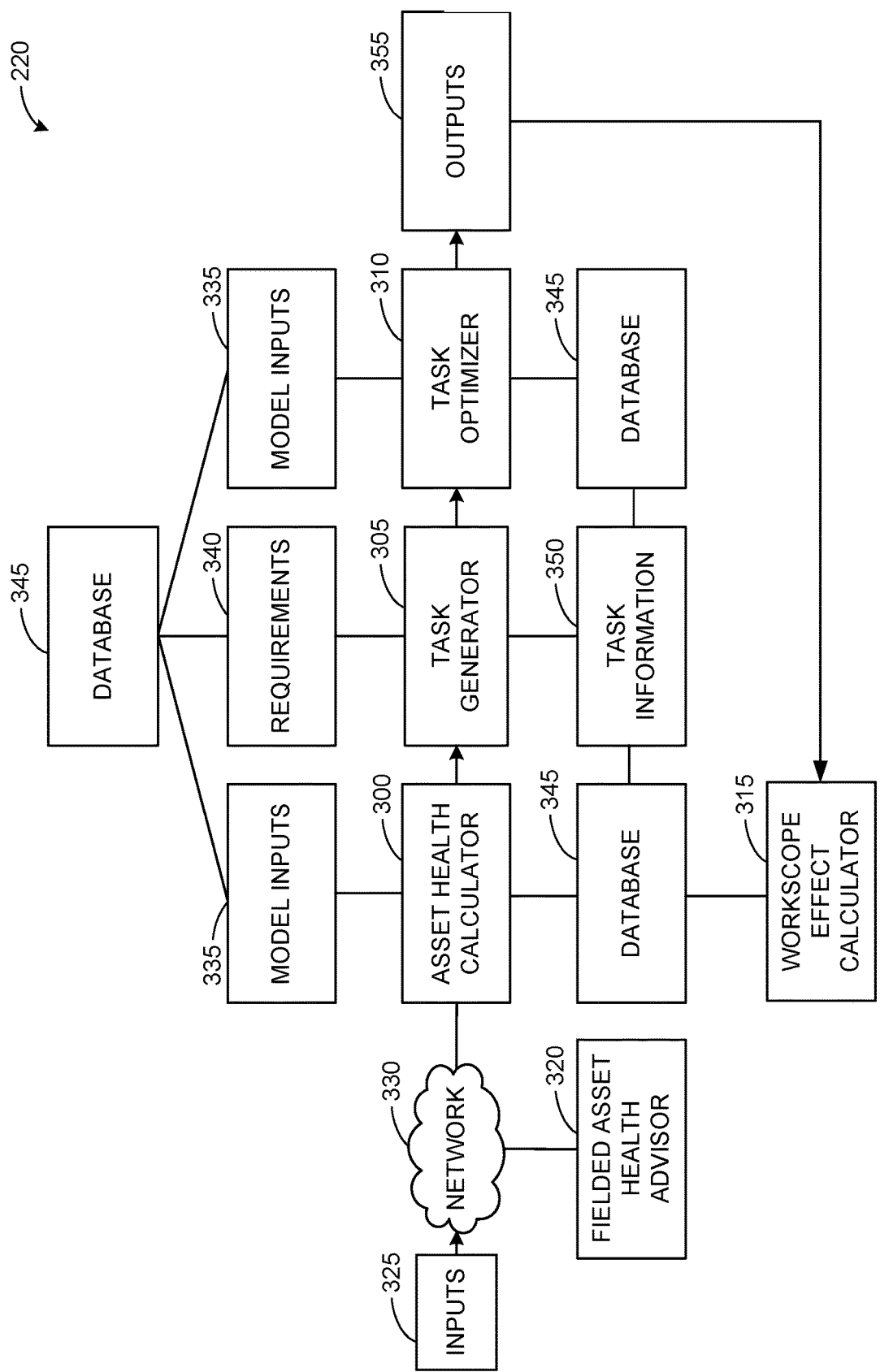
FIG. 3 is a block diagram of an example implementation of the example asset workscope generation system of FIG. 2.

FIG. 3 is a block diagram of an example implementation of the example AWGS 220 of FIG. 2. The example AWGS 220 includes an example asset health calculator 300, an example task generator 305, an example task optimizer 310, an example workscope effect calculator 315, an example fielded asset health advisor (FAHA) 320, example inputs 325, an example network 330, example model inputs 335, example requirements 340, an example database 345, example task information 350, and example outputs 355.

In the illustrated example of FIG. 3, the AWGS 220 includes the example asset health calculator 300 to identify a target asset such as the engine 102 of FIG. 1 for removal to perform a task to improve an operating condition of the target asset. In some examples, the asset health calculator 300 calculates an actual asset health quantifier (AHQ) of an asset based on the inputs 325 (e.g., asset sensor data, engine control inputs, etc.) obtained via the network 330. The example network 330 can implement or correspond to the example network 240 of FIG. 2. For example, the asset health calculator 300 can obtain inputs based on an inspection of the asset by an asset maintenance technician. In another example, the asset health calculator 300 can obtain asset information from the turbine engine controller 100 of the engine 102 of FIGS. 1-2 via the AWGS direct connection 230 of FIG. 2, the AWGS network connection 250 of FIG. 2, the wireless communication links 270 of FIG. 2, etc.

In some examples, the asset health calculator 300 calculates a projected AHQ based on the model inputs 335. For example, the asset health calculator 300 can estimate an operating condition of the engine 102 after the engine 102 completes a specified number of cycles (e.g., flight cycles, operation cycles, etc.). For example, the asset health calculator 300 can simulate the engine 102 completing the specified number of flight cycles by executing a digital twin model of the engine 102 for the specified number of flight cycles. As used herein, the term "flight cycle" refers to a complete operation cycle of an aircraft flight executed by an asset including a take-off operation and a landing operation.

As used herein, the term "digital twin" refers to a digital representation, a digital model, or a digital "shadow" corresponding to a digital informational construct about a physical system. That is, digital information can be implemented as a "twin" of a physical device/system (e.g., the engine 102, etc.) and information associated with and/or embedded within the physical device/system. The digital twin is linked with the physical system through the lifecycle of the physical system. In certain examples, the digital twin includes a physical object in real space, a digital twin of that physical object that exists in a virtual space, and information linking the physical object with its digital twin. The digital twin exists in a virtual space corresponding to a real space and includes a link for data flow from real space to virtual space as well as a link for information flow from virtual space to real space and virtual sub-spaces. The links for data flow or information flow correspond to a digital thread that represents a communication framework between sources of data and the digital twin model. The digital thread can enable an integrated view of asset data throughout a lifecycle of the asset. For example, the digital twin model can correspond to the virtual model of the asset and the digital thread can represent the connected data flow between an asset data source and the virtual model.

In some examples, the asset health calculator 300 identifies a target asset for removal based on comparing an actual AHQ to an actual AHQ threshold and identifying the target asset for removal based on the comparison. In some examples, the asset health calculator identifies a target asset for removal based on comparing a projected AHQ to a projected AHQ threshold and identifying the target asset for removal based on the comparison. In some examples, the asset health calculator 300 generates a removal schedule for one or more target assets based on requirements such as contractual requirements, maintenance resources, spare part inventory, etc., and/or a combination thereof.

In some examples, the AHQ threshold (e.g., the actual AHQ threshold, the projected AHQ threshold, etc.) of an asset, an asset component, etc., represents an indicator, which when satisfied, corresponds to the asset, the asset component, etc., being identified as a candidate for removal to perform maintenance, service, etc. For example, the asset health calculator 300 can compare an actual AHQ of 50 cycles (e.g., flight cycles, flight operations, etc.) remaining (e.g., until service can be performed, until the asset component is taken off-wing, etc.) for the booster compressor 114 of FIG. 1 to an actual AHQ threshold of 100 cycles remaining and identify the booster compressor 114 of FIG. 1 as a candidate for removal based on the actual AHQ being less than the actual AHQ threshold. In another example, the asset health calculator 300 can compare an actual AHQ of 200 hours operating remaining for the booster compressor 114 of FIG. 1 to an actual AHQ threshold of 250 hours operating remaining and identify the booster compressor 114 of FIG. 1 as a candidate for removal based on the actual AHQ being less than the actual AHQ threshold. For example, the actual AHQ threshold, the projected AHQ threshold, etc., can be determined based on a contractual requirement, historical-based information of previously repaired assets and/or asset components, etc.

In the illustrated example of FIG. 3, the AWGS 220 includes the task generator 305 to generate a workscope task for the target asset based on obtaining an AHQ from the asset health calculator 300. For example, the task generator 305 can obtain an AHQ for the engine 102, an AHQ for the booster compressor 114 of the engine 102, etc. In some examples, the task generator 305 identifies an asset component to be processed based on comparing an AHQ to an AHQ threshold and identifying the asset component based on the comparison. For example, the task generator 305 can compare an actual AHQ of 30% useful life remaining for the booster compressor 114 to an actual AHQ threshold of 50% useful life remaining and identify the booster compressor 114 for replacement based on the actual AHQ being less than the actual AHQ threshold.

In some examples, the task generator 305 identifies an asset component to be processed based on the requirements 340 obtained from the database 345. For example, the task generator 305 can compare an actual AHQ of 100 cycles for the booster compressor 114 to an actual AHQ threshold of 200 cycles for the booster compressor 114 based on contractual requirements (e.g., a contract specifies that a booster compressor must be serviced when the actual AHQ goes below 200 cycles). In such an example, the task generator 305 can identify the booster compressor 114 for processing based on the actual AHQ being less than the actual AHQ threshold.

In response to identifying one or more asset components to be processed, the example task generator 305 can generate a set of workscope tasks that can be performed on the one or more asset components. For example, the task generator 305 can determine the set of tasks based on obtaining the task information 350 from the database 345. For example, the task generator 305 can query the database 345 with the identified component for processing (e.g., the booster compressor 114) and the actual AHQ of the component, and the database 345 can return task information including a list of tasks that can be performed with corresponding costs (e.g., labor costs, monetary costs, etc.), spare parts, tools, etc., for each task in the list.

In the illustrated example of FIG. 3, the AWGS 220 includes the task optimizer 310 to identify an optimized and/or otherwise improved workscope for a target asset based on the generated workscope tasks for the target asset and the model inputs 335. For example, the task optimizer 310 can generate a plurality of workscopes in which each workscope includes a combination of one or more of the workscope tasks obtained from the task generator 305. In such an example, the task optimizer 310 can store the plurality of workscopes in the database 345.

In some examples, the task optimizer 310 calculates an estimate asset health quantifier for the target asset to generate quantifiable metrics to evaluate an accuracy or an efficiency of the AWGS 220 in improving an operating condition of the engine 102. For example, the task optimizer 310 can calculate an asset health quantifier for the target asset in response to performing a specified workscope on the target asset. For example, the task optimizer 310 can obtain an actual AHQ of the target asset calculated by the asset health calculator 300, select a workscope of interest for the target asset, and calculate an estimate AHQ of the target asset if the selected workscope were to be performed on the target asset. In some examples, the workscope effect calculator 315 calculates an actual AHQ of the target asset after the selected workscope is completed on the target asset and compares the actual AHQ to the estimate asset health quantifier calculated by the task optimizer 310 to determine an accuracy of the AWGS 220 based on the comparison.

In some examples, the task optimizer 310 calculates an estimate AHQ by executing one or models such as a digital twin model of the target asset to generate the model inputs 335. For example, a digital twin model can be implemented using an artificial neural network and/or other machine learning/artificial intelligence to form connections between inputs and outputs and drive evaluation and behavior through patterns, feedback, optimization, etc.

In some examples, the task optimizer 310 calculates an estimate asset health quantifier for each one of the generated workscopes. In some examples, the task optimizer 310 selects a workscope to be performed on the target asset based on one or more factors such as comparisons of the calculated estimate asset health quantifiers to contractual requirements, customer requirements, operational constraints, etc., and/or a combination thereof. In such examples, the outputs 355 correspond to the selected workscope including a set of tasks to be performed on the target asset and corresponding workscope information. For example, the workscope information can include an assignment of maintenance personnel, a service facility, spare parts, tools, etc., to the workscope based on a removal schedule identified by the asset health calculator 300.

In the illustrated example of FIG. 3, the AWGS 220 includes the workscope effect calculator 315 to generate a predictive asset health quantifier of a turbine engine. For example, the workscope effect calculator 315 can determine one or more de-rate parameters of the turbine engine based on the inputs 325. For example, the workscope effect calculator 315 can determine a value for a takeoff de-rate parameter, a climb de-rate parameter, etc., of the engine 102. The example workscope effect calculator 315 can analyze the de-rate parameters to identify opportunities for increasing TOW, lowering turbine engine maintenance cost, etc., of the engine 102 while respecting operator metrics (e.g., fuel burn, mission times, etc.).

In some examples, the workscope effect calculator 315 generates asset and/or asset component performance and severity models based on the deviations. For example, the workscope effect calculator 315 can translate the impact of environmental factors, operational factors, etc., to asset and/or asset component health factors that drive maintenance operations of the asset and/or the asset components. In some examples, the workscope effect calculator 315 generates a severity model using historical information. For example, the workscope effect calculator 315 can generate an asset health quantifier of an asset component as a function of TOW and an environmental or an operational condition. For example, the workscope effect calculator 315 can generate a severity model that maps TOW of an asset component such as a high-pressure compressor to one or more environmental parameters of significance to component life (e.g., TOW, etc.).

In some examples, the workscope effect calculator 315 generates recommendations to optimize and/or otherwise improve operator behavior corresponding to takeoff de-rate parameters, climb de-rate parameters, etc., when the asset is on-wing of an aircraft. For example, the workscope effect calculator 315 can generate a recommendation to adjust the operator behavior to increase TOW and improve turbine engine performance. For example, the workscope effect calculator 315 can generate a recommendation to change a climb time, a taper schedule (e.g., a turbine engine de-rate taper schedule, etc.), a de-rate parameter, etc., of the asset when on-wing of the aircraft. As used herein, the term "taper schedule" refers to a scheduled de-rating operation of a turbine engine as the turbine engine transitions between flight segments of a flight cycle. For example, the taper schedule can include instructions to operate the turbine engine at 5% de-rate during a takeoff and departure flight segment, at 15% de-rate during a climb flight segment, and at 40% de-rate during a cruise flight segment.

In some examples, the workscope effect calculator 315 generates a report including the recommendations. For example, the workscope effect calculator 315 can generate a report including a candidate improvement plan for identified operators as candidate improvement targets. For example, the candidate improvement plan can include a recommendation to change the climb time, the taper schedule, the de-rate parameter, etc., of the asset when on-wing of the aircraft. In some examples, the workscope effect calculator 315 generates an alert dashboard (e.g., an alert dashboard in a report, an alert dashboard in a web-based software application, etc.) indicating areas of improvement for an operator to improve TOW and to reduce maintenance cost of an asset.

In some examples, the workscope effect calculator 315 calculates an effect of performing a workscope on a target asset. In some examples, the workscope effect calculator 315 calculates a workscope quantifier which represents an accuracy or an efficiency of the AWGS 220 in improving an operating condition of the engine 102. In some examples, the workscope effect calculator 315 calculates an actual AHQ of the target asset in response to the selected workscope being performed on the target asset. In some examples, the workscope effect calculator 315 calculates the actual AHQ based on an inspection (e.g., a visual inspection, etc.) from maintenance personnel, sensor data from the sensors 144, 146 of FIG. 2, etc., and/or a combination thereof. For example, the workscope effect calculator 315 can calculate an actual AHQ of the high-pressure turbine 120 based on comparing (1) a first pressure value and/or a first temperature value of the high-pressure turbine 120 obtained from the sensors 144, 146 of FIG. 2 prior to the selected workscope being performed to (2) a second pressure value and/or a second temperature value of the high-pressure turbine 120 obtained from the sensors 144, 146 after the selected workscope being performed. In such an example, the workscope effect calculator 315 can calculate the actual AHQ based on the comparison.

In some examples, the workscope effect calculator 315 calculates a workscope quantifier based on comparing a first asset health quantifier of a target asset to a second asset health quantifier of the target asset. For example, the workscope effect calculator 315 can calculate a workscope quantifier based on a first actual AHQ calculated by the task optimizer 310 prior to a workscope being performed on the engine 102 and a second actual AHQ calculated by the workscope effect calculator 315 after a completion of the workscope. For example, the workscope quantifier can be a difference between the first and the second actual AHQ, a ratio of the first and the second actual AHQ, etc. For example, the workscope effect calculator 315 can calculate a workscope quantifier of 10% based on a difference between a first actual AHQ of 90% calculated by the task optimizer 310 and a second actual AHQ of 80% calculated by the workscope effect calculator 315 (e.g., 10%=90%−80%, etc.). In such an example, the workscope effect calculator 315 can determine that the AWGS 220 can be improved because the selected workscope did not improve an operating condition of the engine 102 to a level anticipated by the AWGS 220.

In some examples, the workscope effect calculator 315 modifies one or more components of the AWGS 220 based on the operator behavior (e.g., a de-rating behavior of owner assets, etc.). In some examples, the workscope effect calculator 315 modifies the one or more components of the AWGS 220 by calculating a workscope quantifier, comparing the workscope quantifier to a workscope quantifier threshold, and determining whether the workscope quantifier satisfies the workscope quantifier threshold based on the comparison. In some examples, the workscope quantifier threshold represents an indicator which, when satisfied, identifies that the AWGS 220 can be improved by updating one or more components of the AWGS 220. For example, the workscope effect calculator 315 can obtain a first actual AHQ for the booster compressor 114 from the database 345 corresponding to an actual AHQ of 90% useful life remaining calculated by the task optimizer 310. The example workscope effect calculator 315 can generate a second actual AHQ of 70% useful life remaining based on an inspection of the booster compressor 114, the sensor data from the sensors 144, 146, etc.

The example workscope effect calculator 315 can calculate a workscope quantifier of 20% based on calculating a difference between the first and the second actual AHQ (e.g., 20%=90%−70%, etc.). In another example, the workscope effect calculator 315 can calculate a workscope quantifier of 0.78 based on calculating a ratio of the first and the second actual AHQ (e.g., 0.78=0.70÷0.90, etc.). In such an example, the workscope effect calculator 315 can compare the workscope quantifier of 0.78 to a workscope quantifier threshold of 0.85 and determine whether the workscope quantifier satisfies the workscope quantifier threshold. For example, the workscope effect calculator 315 can determine to modify a component of the AWGS 220 based on the workscope quantifier being less than the workscope quantifier threshold.

In response to determining that the workscope quantifier satisfies the workscope quantifier threshold, the example workscope effect calculator 315 can regenerate the example asset health calculator 300, the example task generator 305, the example task optimizer 310, the example model inputs 335, the example requirements 340, the example database 345, the example task information 350, etc., and/or a combination thereof. For example, the workscope effect calculator 315 can direct a digital twin model of the engine 102 to update to a latest version of the digital twin model incorporating up-to-date historical trend information, model parameters, model algorithms, etc. In another example, the workscope effect calculator 315 can direct the database 345 to update to include a latest version of the task information 350. In yet another example, the workscope effect calculator 315 can direct the task optimizer 310 to update one or more algorithms, calculation parameters, etc., used by the task optimizer 310 to a latest version.

In the illustrated example of FIG. 3, the AWGS 220 includes the FAHA 320 to generate a recommendation to improve operational usage of an asset. In the illustrated example, the FAHA 320 includes the asset health calculator 300. In some examples, the FAHA 320 obtains sensor data from the sensors 144, 146 of FIG. 2, model information (e.g., outputs from a physics-based model of an asset, a stochastic model of an asset, etc.), etc., to generate analytics and diagnostics corresponding to a health of the asset. For example, the FAHA 320 can be a software application executing on a computing device (e.g., a desktop computer, a tablet, a smartphone, etc.) to generate asset health information (e.g., an actual AHQ, a projected AHQ, etc.), asset usage recommendations, etc. In other examples, the FAHA 320 can be implemented as a dedicated hardware device (e.g., an application-specific integrated circuit, firmware device, etc.) to monitor asset operation and generate asset health information, asset usage recommendation, etc.

In the illustrated example, the FAHA 320 is communicatively coupled to the network 330. For example, the FAHA 320 can obtain sensor data from the sensors 144, 146, obtain an up-to-date version of one or more models, obtain an up-to-date version of an algorithm or a calculation parameter used by the asset health calculator 300, etc., via the network 330. Alternatively, the example FAHA 320 may not be communicatively coupled to the network 330.

In the illustrated example of FIG. 3, the AWGS 220 includes the database 345 to record data (e.g., asset health quantifiers, workscope quantifiers, the inputs 325, the model inputs 335, the requirements 340, the task information 350, etc.). In the illustrated example, the database 345 is communicatively coupled to the asset health calculator 300, the task generator 305, the task optimizer 310, the workscope effect calculator 315, and the FAHA 320 (e.g., when communicatively coupled to the network 330, etc.). The example database 345 can respond to queries for information related to data in the database 345. For example, the database 345 can respond to queries for additional data by providing the additional data (e.g., the one or more data points), by providing an index associated with the additional data in the database 345, etc. The example database 345 can additionally or alternatively respond to queries when there is no additional data in the database 345 by providing a null index, an end of database identifier, etc. For example, the asset health calculator 300 can query the database 345 for asset sensor data, asset environmental data, utilization data, etc., corresponding to the engine 102. In response to the query, the example database 345 can transmit the data and corresponding information such as data logs, maintenance history, etc., to the example asset health calculator 300.

The example database 345 can be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., flash memory). The example database 345 can additionally or alternatively be implemented by one or more double data rate (DDR) memories, such as DDR, DDR2, DDR3, DDR4, mobile DDR (mDDR), etc. The example database 345 can additionally or alternatively be implemented by one or more mass storage devices such as hard disk drive(s), compact disk drive(s) digital versatile disk drive(s), solid-state drives, etc. While in the illustrated example the database 345 is illustrated as a single database, the database 345 can be implemented by any number and/or type(s) of databases.

While an example implementation of the AWGS 220 of FIG. 2 is illustrated in FIG. 3, one or more of the elements, processes and/or devices illustrated in FIG. 3 may be combined, divided, re-arranged, omitted, eliminated and/or implemented in any other way. Further, the example asset health calculator 300, the example task generator 305, the example task optimizer 310, the example workscope effect calculator 315, the example FAHA 320, the example inputs 325, the example network 330, the example model inputs 335, the example requirements 340, the example database 345, the example task information 350, the example outputs 355 and/or, more generally, the example AWGS 220 of FIG. 3 may be implemented by hardware, software, firmware and/or any combination of hardware, software and/or firmware. Thus, for example, any of the example asset health calculator 300, the example task generator 305, the example task optimizer 310, the example workscope effect calculator 315, the example FAHA 320, the example inputs 325, the example network 330, the example model inputs 335, the example requirements 340, the example database 345, the example task information 350, the example outputs 355 and/or, more generally, the example AWGS 220 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example asset health calculator 300, the example task generator 305, the example task optimizer 310, the example workscope effect calculator 315, the example FAHA 320, the example inputs 325, the example network 330, the example model inputs 335, the example requirements 340, the example database 345, the example task information 350, and/or the example outputs 355 is/are hereby expressly defined to include a non-transitory computer readable storage device or storage disk such as a memory, a digital versatile disk (DVD), a compact disk (CD), a Blu-ray disk, etc. including the software and/or firmware. Further still, the example AWGS 220 of FIG. 2 may include one or more elements, processes and/or devices in addition to, or instead of, those illustrated in FIG. 3, and/or may include more than one of any or all of the illustrated elements, processes and devices.

Figure 4:
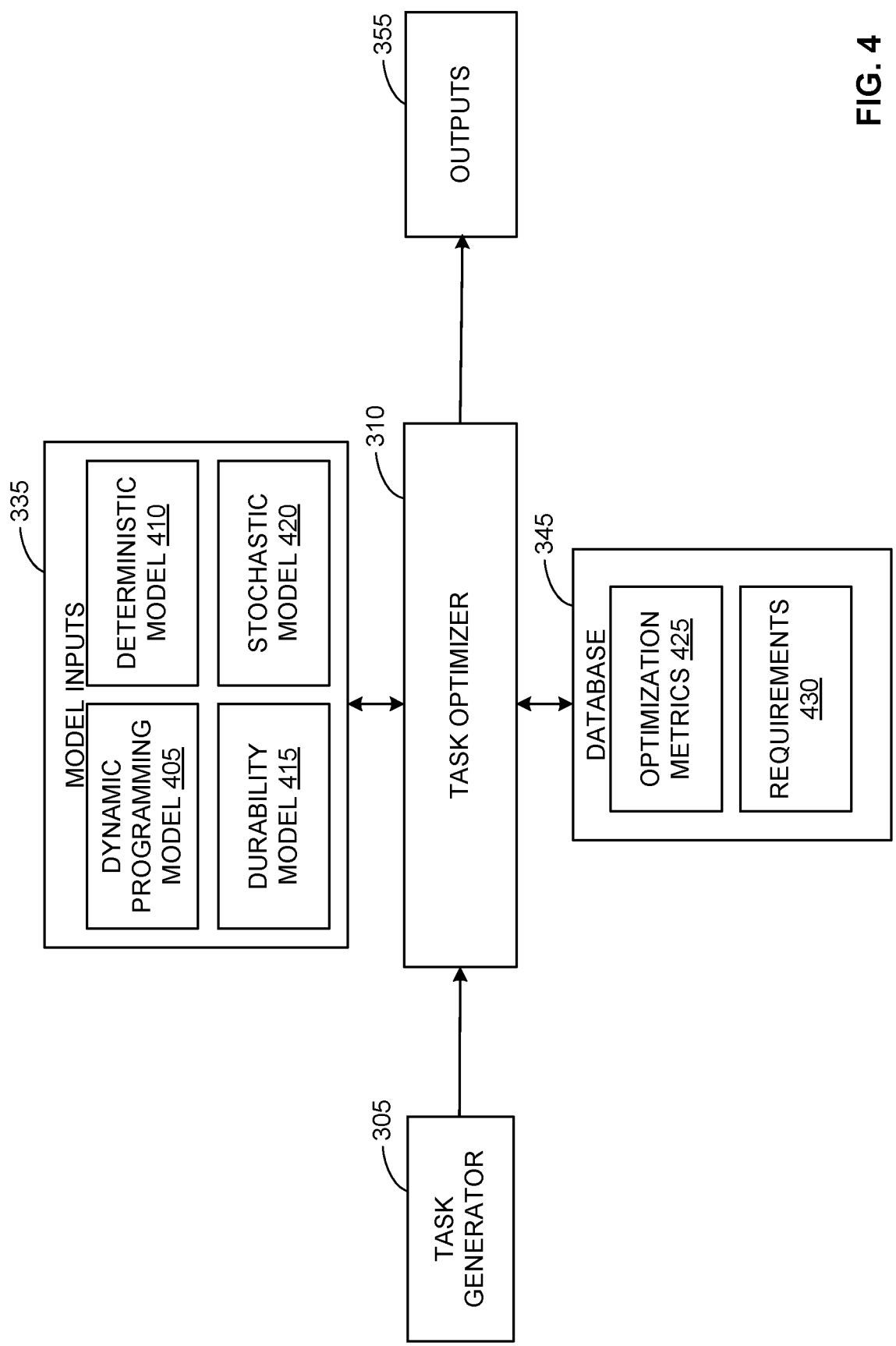
FIG. 4 is a block diagram of an example implementation of a portion of the example asset workscope generation system of FIGS. 2-3.

FIG. 4 is a block diagram of an example implementation of a portion of the AWGS 220 including the task generator 305, task optimizer 310, model inputs 335, database 345, and outputs 355. As shown in the example of FIG. 4, the model inputs 335 include a plurality of models including a dynamic programming model 405, a deterministic model 410, a durability model 415, and a stochastic model 420. In the illustrated example of FIG. 4, the database 345 includes optimization metrics 425 and requirements and/or other constraints 430 such as contract requirements (e.g., contract model), engine data, workscope drivers, etc., gathered from a service contract input, engine asset monitoring data, asset digital twin feedback, service bulletins, degradation/damage information, etc., and stored in/streamed to the database 345. The model inputs 335 and database 345 provide input to the task optimizer 310 to generate an optimized and/or otherwise improved workscope as output 355.

For example, time on wing and shop cost for a target asset are related by workscope. Balancing Customized Service Agreement (CSA) durability, operability and performance requirements with financial metrics is a multidimensional optimization problem with millions of solutions. The task optimizer 310 analyzes possibilities and presents top candidates based on input criteria including the dynamic programming model 405, deterministic model 410, durability model 415, and/or stochastic model 420, etc. Evaluating all the possibilities manually is impossible.

The task optimizer 310 provides rapid, consistent and unbiased evaluation of workscope scenarios with respect to restrictions and constraints such as contract profitability and terms and conditions (e.g., time horizon, rates, limits on time between asset component maintenance, and/or other soft and hard constraints). Through evaluation of workscope scenarios/options, the task optimizer 310 avoids putting unnecessary workscope(s) into an engine (e.g., depending on optimization objective function(s) chosen, etc.), for example. Further, the task optimizer 310 identifies additional workscoping opportunities where additional workscope may be beneficial. The example task optimizer 310 facilitates analytics-based removal (e.g., on wing) and analytics-based workscoping (e.g., off wing).

In certain examples, the task optimizer 310 leverages task generator 305 input along with model information 335 and database information 345 to determines a minimum workscope for a current shop visit based on the requirements 430 and health of components. For example, the task generator 305 provides a list or set of potential maintenance operations that can be completed within a next shop visit and/or subsequent shop visit(s) for a target asset. Each maintenance operation includes one or more tasks, where each task has corresponding information (e.g., a workscope level, etc.) such as type and quantity of personnel to complete task, components and/or tools needed to complete task, time and cost to complete task, etc. Each maintenance operation can be assigned a criticality index, modifier, or quantifier to drive a minimum and/or otherwise reduced workscope by weighing a maintenance operation with respect to other maintenance operation(s), for example.

The task optimizer 310 identifies possible additional tasks for the minimum workscope and associated costs of the additional tasks. The task optimizer 310 calculates when future shop visits will occur during a contract using the dynamic programing models 405. The task optimizer 310 identifies future workscopes for the future shop visits and associated costs. The task optimizer 310 analyzes all possible workscopes and costs using a dynamic programming solution. The task optimizer 310 selects optimal workscope(s) for the current shop visit that satisfies contract requirements 430 and reduces or minimizes expected costs and/or increases time on wing through the end of the contract, for example. Put another way, the task optimizer 310 selects a workscope having the best/most value (e.g., based on cost of repairs versus income from contract payments over a contractual horizon time, etc.) with respect to restrictions and/or constraints on the target asset.

Using the task optimizer 310, a workscope is determined based on multiple inputs including cumulative damage models of parts, modules, and systems, statistical models (e.g., parametric (e.g., Weibull probability distribution, etc.) and/or non-parametric), financial models, contract term, conditions, and/or customer expectations, etc. The task optimizer 310 processes the model inputs 335 to evaluate a financial impact of a series of possible workscopes over the life of a service contract to facilitate creation of an optimized or otherwise improved workscope selection with associated predicted outcomes.

The task optimizer 310 obtains specific contract information, maps failure mode distributions to one or more workscoping models, and constructs a workscoping model with associated price, cost and billing structure. For a given shop visit, the task optimizer 310 computes failure mode probabilities with workscope options using a dynamic optimization approach which is propagated to end of the contract.

Figure 5:
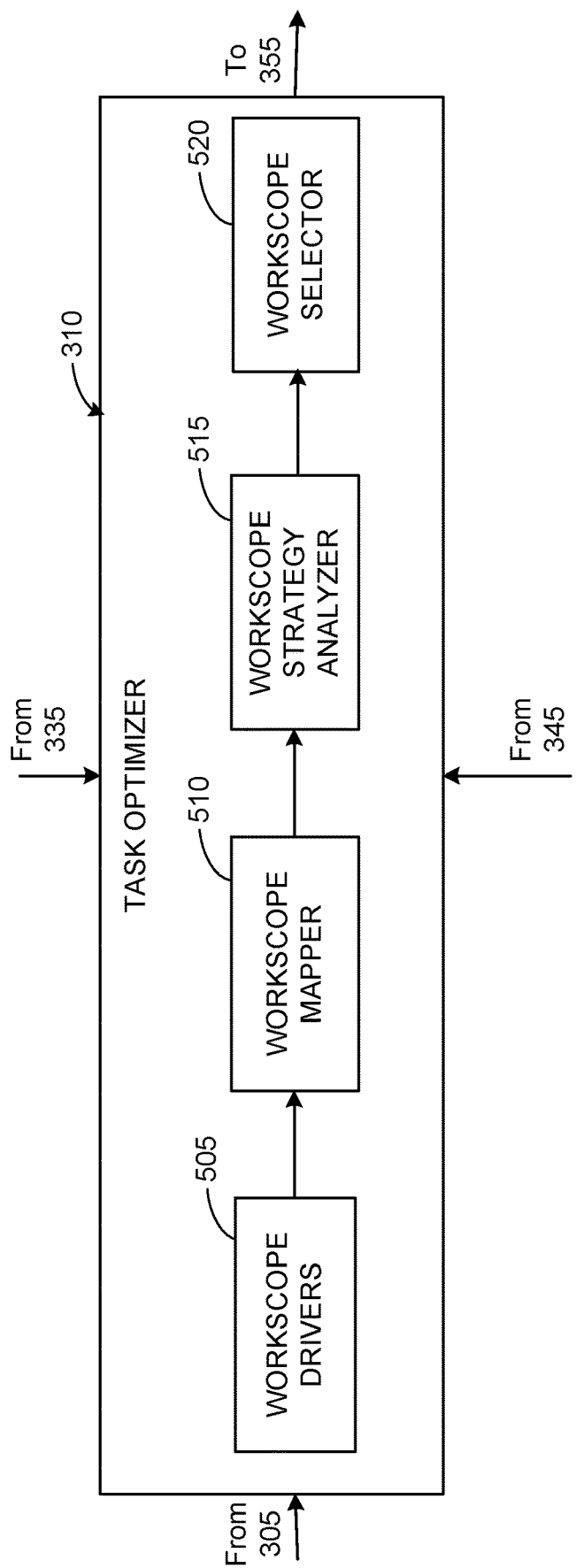
FIG. 5 is a block diagram of an example implementation of the example task optimizer of FIGS. 3-4.

FIG. 5 is a block diagram of an example implementation of the example task optimizer 310 of FIG. 3. In the illustrated example of FIG. 5, the task optimizer 310 includes workscope drivers 505, a workscope mapper 510, a workscope strategy analyzer (WSA) 515, and a workscope selector 520. The task optimizer 310 receives a combination of one or more tasks in the workscope from the task generator 305 and processes the task(s) to determine one or more workscopes to accomplish the task(s) for a target asset. The task optimizer 310 determines an optimized and/or otherwise improved workscope from the one or more workscopes for execution with respect to the task(s) for the target asset.

Figure 6:
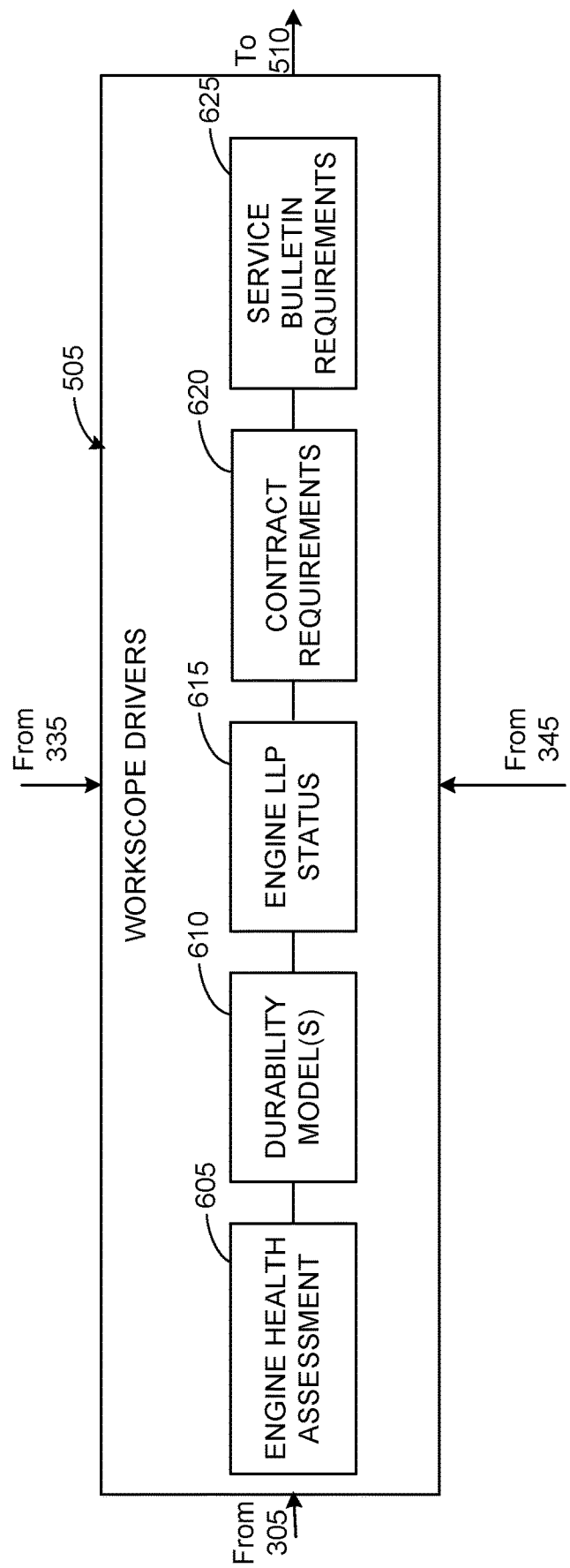
FIG. 6 is a block diagram of an example implementation of the example workscope drivers of FIG. 5.

As shown in the example of FIG. 5, one or more workscope drivers 505 are generated based on input from the model inputs 335 (e.g., dynamic programming model 405, deterministic model 410, durability model 415, stochastic model 420, etc.) and database 345 (e.g., optimization metrics 425, requirements 430, etc.), as well as the task generator 305. As illustrated in the example of FIG. 6, workscope drivers 505 can include an engine health assessment 605, durability model(s) 610, engine life-limited part (LLP) status 615, contract requirements 620, service bulletin (SB) requirements 625, etc.

That is, workscope selection drivers 505 can be used to drive a minimum workscope build that is greater than a minimum total expectation for constraints related to the target asset. LLP time limits and/or other restrictions, SBs, contract terms and conditions greater than popular, restored, and/or hybrid asset workscope tasks can be used to expand or contract a workscope of tasks for maintenance of the target asset, for example. Asset characteristics such as operability (e.g., in accordance with an SB, etc.), durability, performance, etc., can be applied to drive and/or otherwise model workscope tasks. For example, performance of a turbine engine asset can be measured against an exhaust gas temperature (EGT) margin to quantify a minimum performance expectation driving workscope. For example, an EGT margin, which serves as an indicator of engine time on-wing and engine health, is at its highest level when the engine is new or has just been refurbished. An operating margin (e.g., profit with respect to a service contract, etc.) can also be a workscope driver.

For example, the workscope drivers 505 can include a physics-based model such as a digital twin of the engine 102. For example, the digital twin model can simulate physics behavior, a thermodynamic health, a performance health, etc., of the engine 102. For example, the digital twin can simulate inputs and outputs of the sensors 144, 146 of the engine 102. In some examples, the digital twin and/or other physics-based model can simulate an operability of the engine 102 (e.g., an efficiency of the engine 102, etc.), a durability 415 of the engine 102 (e.g., a mechanical stress on the fan section 108, the booster compressor 114, etc.), etc., based on simulating the engine 102 executing one or more flight cycles, flight legs, flight operations, etc.

In certain examples, the stochastic model 420 can represent probability distributions of potential outcomes allowing for random variation in one or more inputs over time. In some examples, the stochastic model 420 generates the random variation based on fluctuations observed in historical data (e.g., the model inputs 335 based on a historical data model, etc.) for a selected time period using time-series techniques. For example, the stochastic model 420 can calibrate the random variation to be within limits set forth by the outputs from the historical data model. In some examples, the stochastic model 420 includes generating continuous probability distributions (e.g., Weibull distributions, reliability curves, etc.) to determine a distribution of failure rates over time due to one or more asset components. For example, the stochastic model 420 can generate a failure rate of the engine 102 based on determining failure rates for the fan section 108, the booster compressor 114, etc., of the engine 102.

In some examples, a hybrid model is formed from one or more of the historical data model, the physics-based model, and the stochastic model 420. For example, the hybrid model can be the stochastic model 420 in which the outputs from the stochastic model 420 are compared to the physics-based model (e.g., the engine digital twin, etc.) and the outputs are adjusted based on the comparison. In another example, the hybrid model can be the stochastic model 420 in which the outputs from the stochastic model 420 can compared to the historical data model and the outputs are adjusted or calibrated based on the comparison.

The workscope drivers 505 provide input to the workscope mapper 510, which maps a shop visit driver 505, such as failure mode, service bulletin campaign, cumulative damage model, other analytics, etc., to a potential workscope per part, module, subsystem, etc. For example, a system-level workscope can be formed as an aggregate of a minimum or otherwise reduced workscope for each workscope requirement 430. The mapping to a system-level workscope helps ensure that the aggregated workscope is a minimum to restore a required level of capability and/or performance, for example. Workscope drivers 505, such as engine health assessment 605, durability model(s) 610, engine LLP replacement status 615, contract repair limits 620, service bulletin requirements 625, etc., can be applied for each task from the task generator 305 to generate a minimum workscope for each requirement mapped to a total/aggregate workscope at the system, subsystem, module, and/or part level for the target asset.

The workscope mapper 510 can integrate a plurality of shop visit drivers 505, each driver 505 represented by an analytic or logic to be used to drive workscope decisions. For example, each workscope driver 505 is represented by a deterministic time limit for repair/replace and/or a probabilistic distribution of timing for repair/replacement of a part/module/device, etc. A workscope at the deterministic time limit is to restore partially or fully the time cost for a set of parts/modules. For each workscope, a probabilistic distribution of when the next shop visit will happen can be calculated for trade-off analysis. The deterministic time limit and probability of repair/replace can be combined for a more accurate determination of time limit until next repair/replacement, for example, based on drivers 505 such as engine health assessment 605, durability model(s) 610, engine LLP replacement status 615, contract repair limits 620, service bulletin requirements 625, etc.

In certain examples, the workscope mapper 510 maps contract information 620, failure mode distributions (e.g., based on engine health assessment 605, durability model 610, engine LLP status 615, etc.), etc., to a workscoping model. The workscoping model can be represented using a digital twin of the asset (e.g., engine, engine subsystem, engine aspect, engine characteristic, etc.) and/or other artificial neural network, machine learning construct, etc. In certain examples, the workscope mapper 510 is dynamic and adjusts for both predicted and actual feedback regarding target asset health and operations status.

In certain examples, a financial impact can be computed and evaluated over the life of a contract for a target asset assuming a specific workscope combining probability failure modes, discrete events, contract specifications, etc. For example, the WSA 515 can apply one or more mathematical models/equations to compute an expected cost, price, and operating margin over the life of the contract (LOC) for each potential workscope. The WSA 515 facilitates a tradeoff analysis for asset (e.g., engine, etc.) removal and "optimal" or otherwise improved workscope selection, for example. The WSA 515 processes input including contract details such as payment structure, removal scheduling requirements, life limited parts (e.g., actual LLP and/or soft timer and pseudo LLP, etc.), financial considerations (e.g., resale value of used parts, etc.), workscope cost, interdependency of workscope for modules, probability of engine removals due to different workscope drivers and deterministic drivers, etc. For example, the WSA 515 can compute an LOC financial impact for a new asset based on a current maintenance/workscope decision followed by a probability associated with a next decision point and a final outcome over a plurality of cycles. Based on the LOC financial impact, an expected time-on-wing (TOW) for the asset can be determined for a period following a shop visit (SV).

The WSA 515 of the task optimizer 310 provides a maintenance planning optimization tool to optimize and/or otherwise improve maintenance strategies based on customer critical-to-quality (CTQ) characteristic(s) and/or contract profitability, for example. The WSA 515 evaluates current and future consequences of each maintenance decision and considers possible paths with associated probability and value (e.g., cost versus benefit in performance, durability, operability, income, etc.). While there are too many possibilities for human analysis or simulation, the WSA 515 can evaluate possible paths and associated consequences via an analytical solution to optimize and/or otherwise improve maintenance of a fleet of engines and/or other assets, for example.

User input, such as current engine status, optimization metric(s) 425, etc., can be combined with fixed tool inputs such as contract margin review (CMR) (e.g., an annual and/or other periodic contract profitability evaluation based on prior projection, etc.), integrated cost analysis model (ICAM) (e.g., a Weibull-based simulation of shop visit removals and associated cost over the life of the contract, etc.), workscope dependency rules, etc., for use by the WSA 515 to provide an analytical programming solution for workscope optimization. An output of the WSA 515 to the workscope selector 520 can include optimal/improved workscopes, expected revenue, expected cost, expected operating margin, expected LLP financials, probability of future shop visits, likely drivers of future shop visits, expected TOW until future shop visits, etc.

Thus, the WSA 515 quickly calculates and ranks workscope alternatives formed by the workscope mapper 510 based on information from the task generator 305 and workscope drivers 505. Update Weibull and cost information can be provided based on the automated input and can be customized to each contract, for example.

In certain examples, the WSA 515 executes a two-step process to maintenance optimization. First, the WSA 515 automatically collects CMR information. For example, Weibull distributions, costs/prices, sub-fleeting, special contract rules, dependency rules, etc., can be gathered by the WSA 515 from the drivers 505, engine status data, database 345 information, etc., for one or more failure-related tasks, etc.

Then, the WSA 515 processes engine status information. For example, the WSA 515 (e.g., automatically, etc.) processes cycle information (e.g., engine cycles since new (ECSN), engine cycles since shop visit (ECSV), etc.), engine utilization, flight leg, removal cause, LLP information, minimum build, requirements 430 (e.g., maintenance goals, etc.), optimization metrics 425, etc. The WSA 515 can generate a maintenance optimization schedule for one or more workscope alternatives ranked accordingly including revenue, cost, operating margin, etc., based on a current/upcoming shop visit, TOW, etc. A TOW distribution until next shop visit can be graphed and presented for evaluation by the WSA 515 for each workscope alternative over a plurality of cycles (e.g., 2500, 5000, 7500, 10,000, 12,500, 15,000, 17,500, 20,000, etc.). The WSA 515 can also generate one or more probabilistic predictions for a future shop visit according to a shop visit driver such as an engine component (e.g., fan, baffle, other), engine operating characteristic (e.g., exhaust gas temperature (EGT), etc.), etc.

For example, failure data (e.g., a Weibull distribution, cumulative damage model, etc.) can be processed to impact a probabilistic prediction for a future shop visit.

Figure 7:
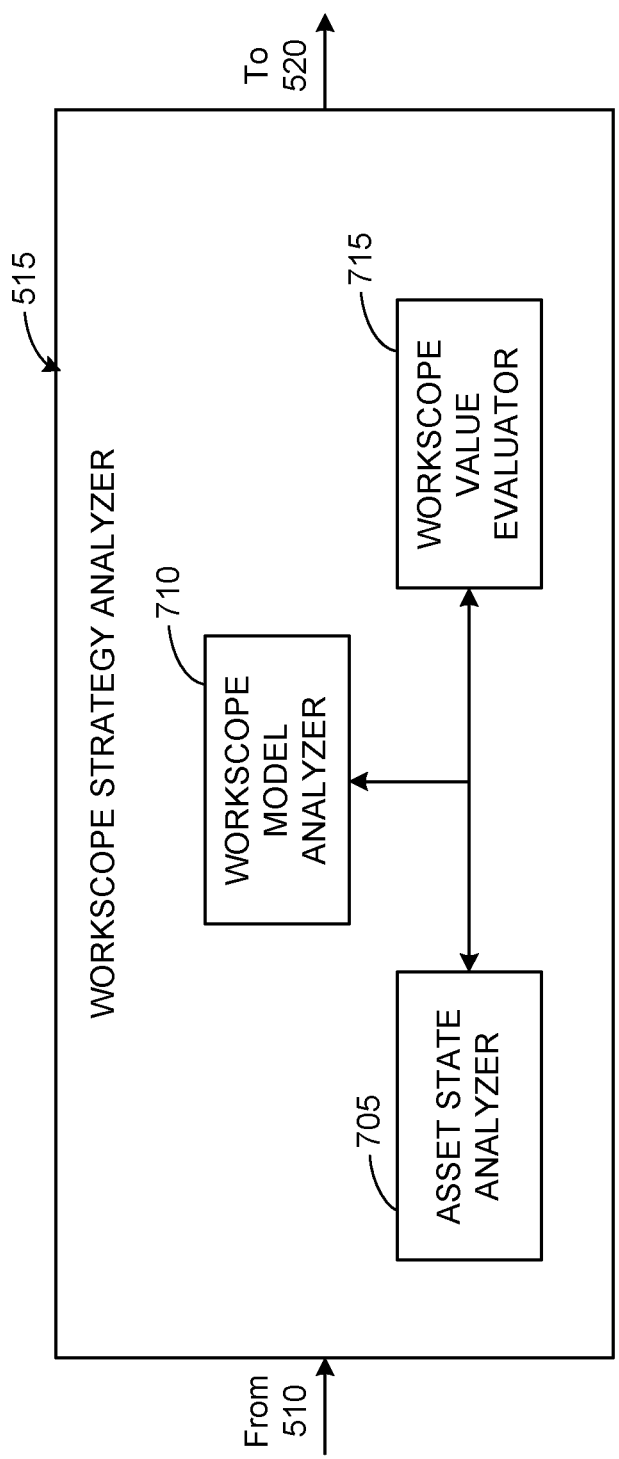
FIG. 7 illustrates an example implementation of the example workscope analyzer of FIG. 5

FIG. 7 illustrates an example implementation of the WSA 515. As shown in the example of FIG. 7, the WSA 515 includes an asset state analyzer 705, a workscope model analyzer 710, and a workscope value evaluator 715. In the example of FIG. 7, the asset state analyzer 705 receives information regarding the target asset (e.g., data regarding an engine, engine subsystem, etc., such as engine status, shop visit driver, LLP status, service bulletin status, etc.), contract model information (e.g., contract type, contract terms and conditions, contract end date, end engine state, etc.). The asset state analyzer 705 processes the received information to provide a state-based solution or model to select among workscope alternatives (e.g., to facilitate selecting an optimal or recommended workscope from the list of available workscopes).

In certain examples, a time interval associated with a service contract for an asset, such as an engine, includes a plurality of stages. A stage indicates a time at which a decision is made (e.g., for a shop visit). A stage begins when a component (e.g., the engine and/or other asset) enters the shop for repair/maintenance/replacement. A state of the asset at a stage indicates a condition of the system at that stage. The state can be quantified based on asset time on engine, time on modules, shop visit driver(s), etc. The state can be used to define a time remaining until the end of the time interval associated with the service contract, as well as the time on each system (e.g., asset) component and identification of a failing component, for example. The state can be defined by a vector quantifying these elements, for example. The asset state analyzer 705 quantifies and provides asset state information to the workscope model analyzer 710 to analyze and compare possible workscopes from the workscope mapper 510 based on asset stage, state, etc.

The example workscope model analyzer 710 analyzes available workscope options provided by the workscope mapper 510 based on models, probabilities, and asset state information from the asset state analyzer 705. For example, the workscope mapper 510 can provide one or more workscopes that are available to be performed on the engine and/or other system asset. Each workscope can define a different set of maintenance activities to be performed on asset component(s) when compared to other workscope(s). In certain examples, a "base" workscope, a "full" workscope, and/or one or more alternative workscopes can be identified and/or otherwise generated as available to be performed on the target asset, such as an engine and/or a subset of its components, related components, etc. In certain examples, a workscope can be referred to as none, heavy, medium, or light based on an associated workscope planning guide and platform. Even a workscope of "none" can include an inspection of the target asset, for example.

In certain examples, the base workscope is a minimal set of maintenance activities to be performed on the engine and/or engine components. Alternatively, the base workscope may be a predetermined or "default" set of repair and/or maintenance activities to be performed on the engine and/or engine components. For example, the base workscope may include only repairing components that have failed and/or that are identified as "life-limited" components or LLP (e.g., parts that are to be replaced and/or repaired within a predetermined time period). Alternative workscopes include additional and/or alternative repair and/or maintenance activities that may be performed on the engine and/or engine components as compared to the activities identified in the base workscope. The full workscope is a full set of maintenance activities to be performed on each component of the system. For example, the full workscope may include performing a maintenance activity on each component of the system when the system and/or components are taken to the maintenance facility, even if the components are not identified as requiring maintenance or repair. The available workscopes (e.g., the base workscope, the full workscope, and/or the alternative workscopes) are transmitted from the workscope mapper 510 to the workscope strategy analyzer 515, for example.

The workscope model analyzer 710 analyzes the available workscopes generated by the workscope mapper 510 based on status information from asset state analyzer 705 including engine data, contract model, status information, etc., to select an "optimal" or improved workscope for execution. In certain examples, an artificial neural network and/or other mesh/graph of decisions and outcomes for a target asset can be used to evaluate a probability of one or more final outcomes.

Figure 8:
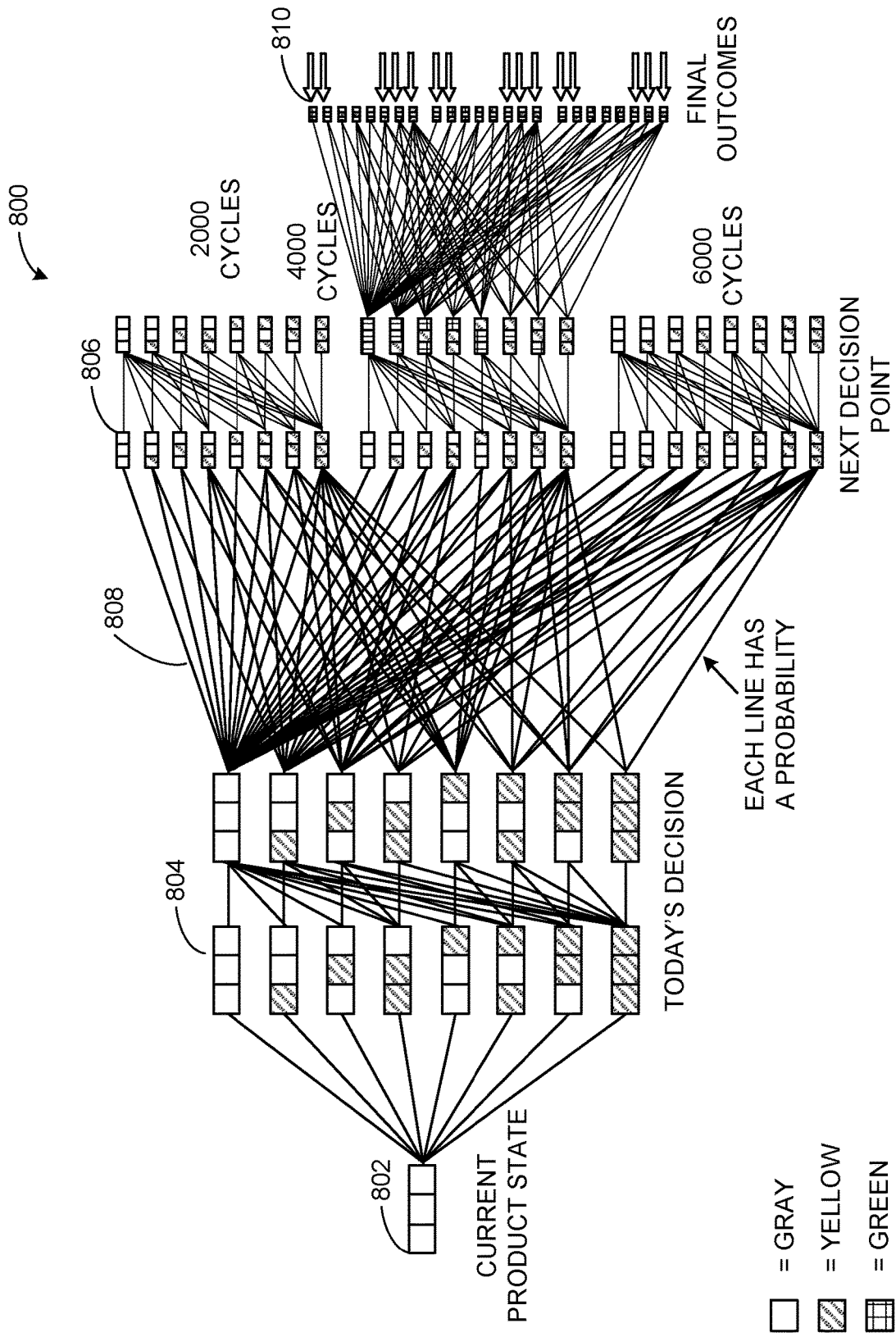
FIG. 8 illustrates an example network of decisions and associated probabilities for a target asset.

For example, as shown in FIG. 8, an asset having a current product state 802 is connected to a plurality of potential decisions 804, 806, and each decision 804, 806 has an associated probability 808. As shown in the example network 800 of FIG. 8, each possible branch or path from a first decision point 804 to a next decision point 806 is associated with a probability 808.

Figure 9A:
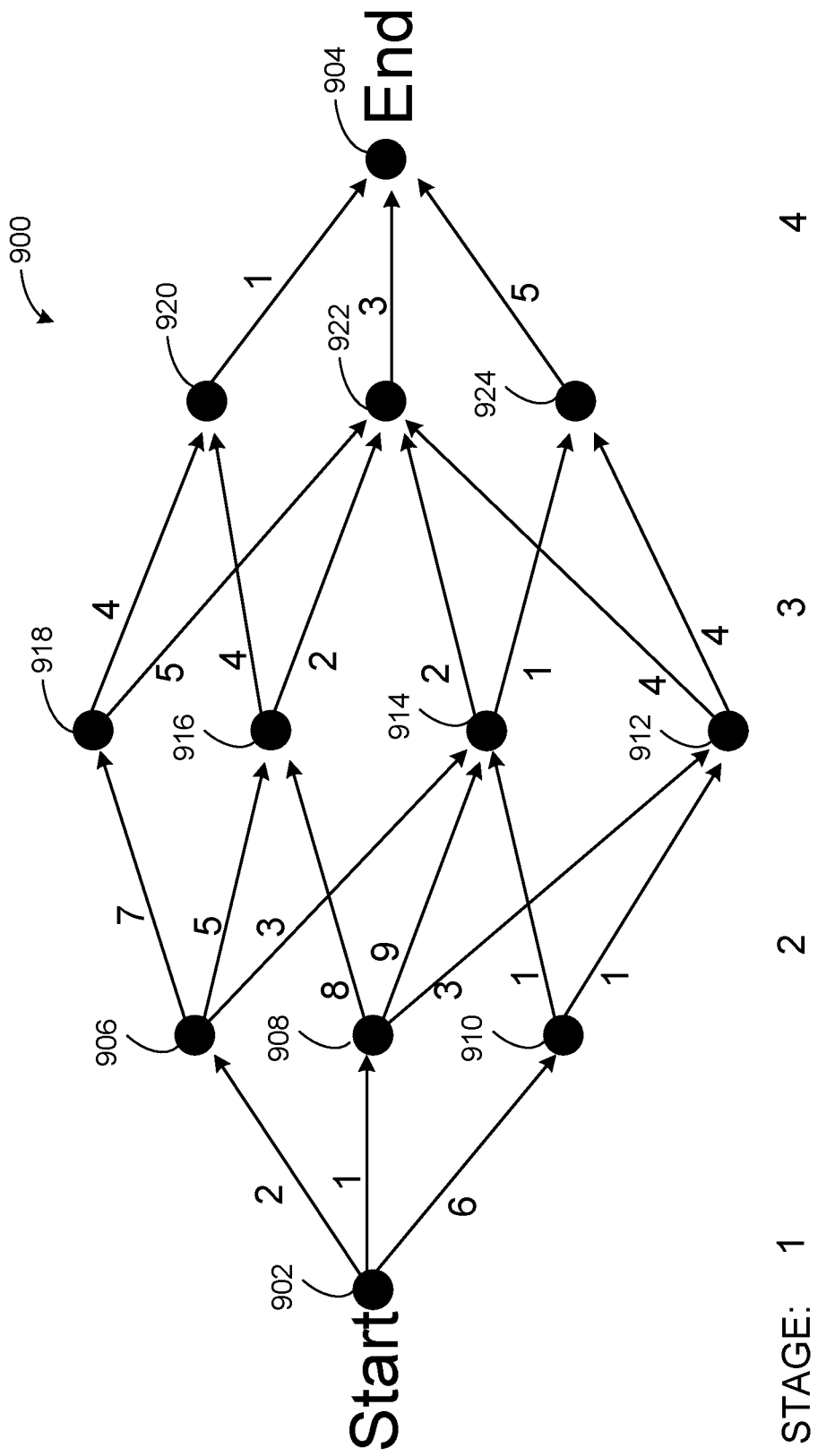
FIGS. 9A-9B illustrate example networks with weighted paths between a starting point and an end point.
Figure 9B:
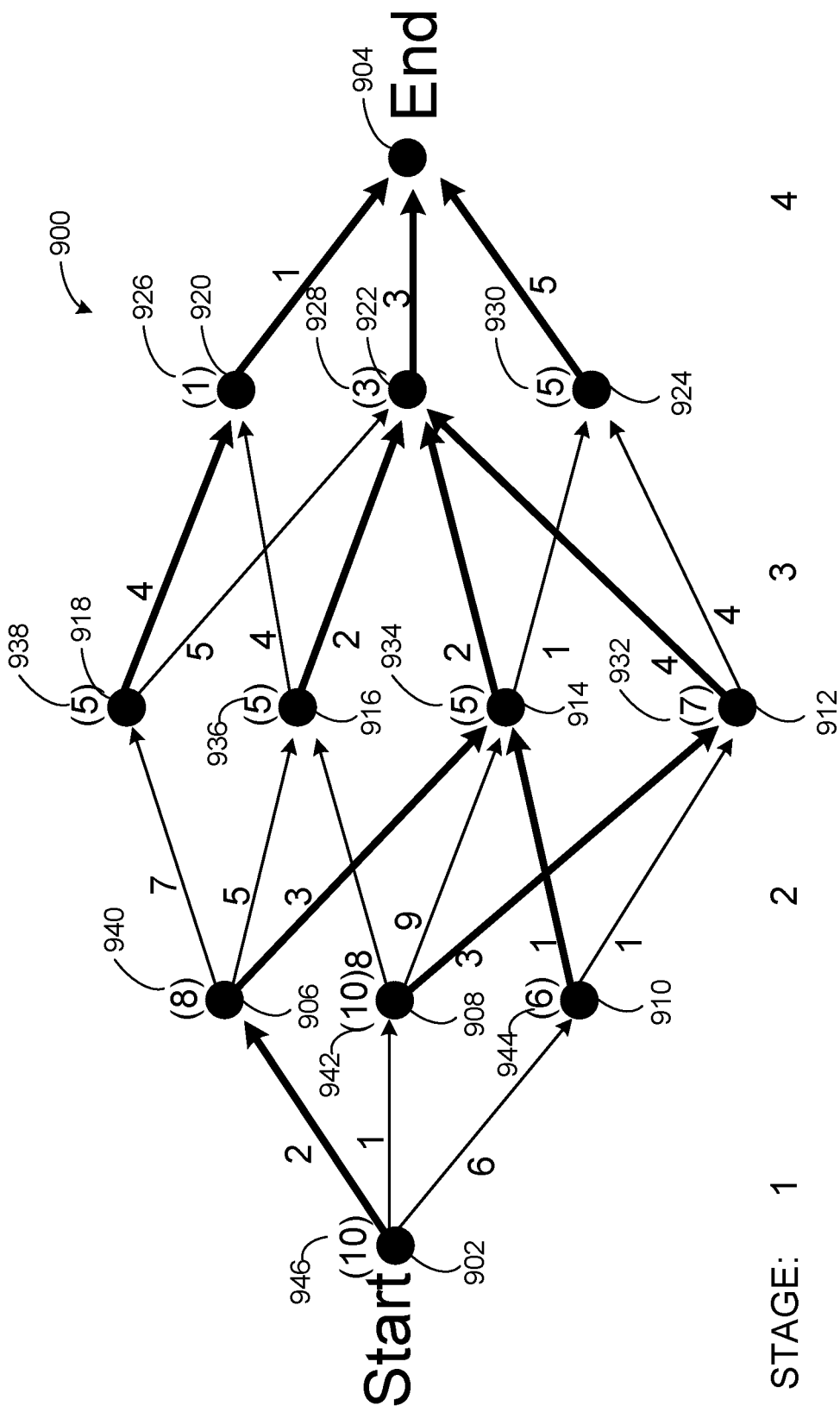

In certain examples, the network is traversed to get from a starting point to an endpoint (e.g., a starting point of an engine service contract to an end point of an engine service contract, etc.) while minimizing a cost to get from the starting point to the end point. For example, as shown in FIG. 9A, a plurality of nodes or decision points representing a time directed discrete probability graph of possible future events (e.g., shop visits, asset failure/damage, etc.) are found in a network 900 between a starting point 902 and an endpoint 904. As shown in the example of FIG. 9B, the workscope model analyzer 710 implements a dynamic programming solution to start at a last stage 4 and move back through the network 900 (e.g., stage 4 to stage 3, stage 3 to stage 2, stage 2 to stage 1). Each node or decision point 902-924 has an associated cost and/or value (e.g., cost versus benefit, and/or other objective function such as maximizing time on-wing, etc.) 926-946. For each state in the stage 4, a minimal path forward is determined as well as a total remaining cost associated with the path. This analysis is repeated for stages 3, 2, and 1 to arrive at a total cost for each state from the starting point 902 to the endpoint 904. A model can implement the example network 900 and be used by the workscope model analyzer 710 to evaluate potential paths and associated costs from start 902 (e.g., engine in service, etc.) to finish 904 (e.g., end-of-life for the engine, etc.). Intermediate nodes 906-924 can represent workscope tasks (e.g., shop visits, etc.) for the asset during the life of the asset, for example. The workscope model analyzer 710 can process the network model 900 in a deterministic and/or stochastic analysis, for example.

In a deterministic analysis, a decision results in a fixed outcome. For example, possible actions include {a, b, c}, such that action a results in a top path in the example network 900, action b results in a middle path in the example network 900, and action c results in a bottom path in the example network 900.

In a stochastic analysis, a decision results in a distribution of possible outcomes. For example, possible actions include {a, b}, such that action a results in a top path with a probability of 0.1, a middle path with a probability of 0.5, and a bottom path with a probability of 0.4. Action b results in the top path with a probability of 0.33, the middle path with a probability of 0.33, and the bottom path with a probability of 0.33, for example.

In certain examples, a discrete stochastic model can be implemented by the workscope model analyzer 710 using stochastic dynamic programming. The example model can be defined as:

$$V_N = \min_{a \in W}\left[C(i, a) + \sum_j P_{ij}(a)V_{N-1}(j)\right], \quad \text{(Eq. 1)}$$
$$\text{for } 0 < N < M,$$

$$V_0 = \min_{a \in W} C(i, a). \quad \text{(Eq. 2)}$$

In Equations 1-2 above, $V_N(i)$ is a minimum expected cost when N stages remain of a total of M stages and the asset is in state I; $C(i,a)$ is a current cost for making decision a when the asset is in state i; $P_{ij}(a)$ is a probability of moving from state i to state j when decision a is made; and W is a set of possible decisions at the given stage and state. Here, according to Equation 2, $V_0(i)=C(i, \text{base Workscope})$.

While Equations 1 and 2 represent the discrete stochastic model, a continuous stochastic model can be generated by replacing the sum with an integral and replacing $P_{ij}$ with a probability density function (PDF):

$$V_N(i) = \min_{a \in W}\left[C(i, a) + \int f(a)V_{N-1}(j)\right], \quad \text{(Eq. 3)}$$
$$\text{for } 0 < N < M,$$

wherein $f(a)$ represents the PDF.

Thus, the workscope model analyzer 710 evaluates a given stage (e.g., a given shop visit (SV), etc.) and associated state (e.g., state 1=age of engine, 2=time on each module, 3=driver of the SV, etc.) to drive a decision identifying which workscope alternative is to be exercised. The workscope value evaluator 715 works with the workscope model analyzer 710 to evaluate associated cost/benefit such as with respect to a cost/profit goal (e.g., to minimize an overall expected cost to end (e.g., 20,000 cycles, 25,000 cycles, 30,000 cycles, 50,000 cycles, etc.). To solve the workscope strategy analysis problem the asset state analyzer 705, workscope model analyzer 710, and workscope value evaluator 715 work together to analyze the models and the data using a stochastic dynamic programming model with continuous states, for example.

For example, a workscope strategy analysis can be divided into M stages (e.g., stages 1-4 corresponding with shop visits 1-4 up to a contract limit (e.g., an end of life of the contract and/or other limit, etc.) of a number of 25,000 cycles (and/or other appropriate target based on the product line, etc.) for the target asset (e.g., engine, engine module, etc.), etc.). If the system is in stage k and is currently in the shop for repair, a probability of reaching the contract limit in M-k or fewer additional shop visits is greater than P, where P is a level of certainty (e.g., P=0.99, etc.).

Thus, using dynamic programming, the WSA 515 can analyze models of available workscope and determine a preferred or "optimal" workscope to be selected from the available workscopes which minimizes or otherwise reduces an expected or average cost and/or provides a best overall value (e.g., cost versus benefit such as income per contract, repair value over contract horizon time, etc.). The workscope value evaluator 715 examines a cost associated with the stages and states of each available workscope as processed by the workscope model analyzer 710 and calculates an average cost for each of the available workscopes that can be selected. Thus, the WSA 515 can compare each available workscope and associated cost/benefit (e.g., workscope value) to select an "optimal" workscope to be executed with respect to the target asset.

Figure 10A:
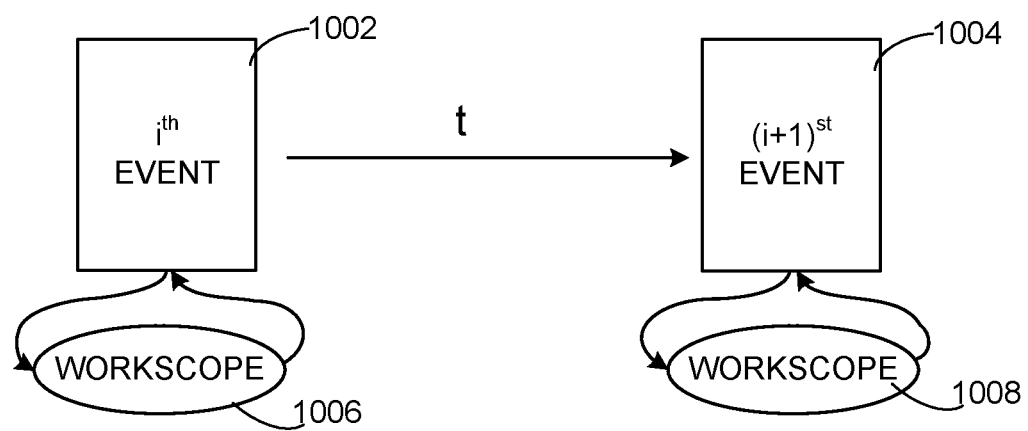
FIGS. 10A-10B illustrate example state-based systems for workscope analysis.

In certain examples, the WSA 515 can be implemented as a state-based system for dynamic workscope analysis. As shown in the example of FIG. 10A, a plurality of events such as an $i^{th}$ event 1002 and a $(i+1)^{st}$ event 1004 are defined and separated by a time t. Each event 1002, 1004 is associated with a workscope 1006, 1008. The time t between the $i^{th}$ and $(i+1)^{st}$ event is based on a state of the asset (e.g., the engine and/or engine module, etc.) when the asset leaves the shop (e.g., time on each module, etc.) and how the asset is operated (e.g., captured in Weibull parameters, etc.). The time t follows a probability distribution and/or density function.

Figure 10B:
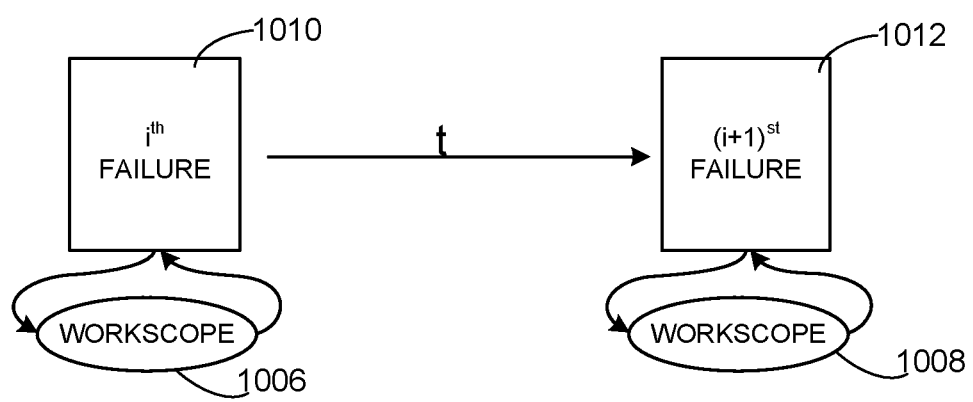

The probability distribution function (and/or probability density function) (PDF) can be associated with a Weibull distribution of failure, as shown in the example of FIG. 10B. An $i^{th}$ failure 1010 is separated from an $(i+1)^{st}$ failure 1012 by the time t. Each failure 1010, 1012 is associated with a workscope 1006, 1008. In the example of FIG. 10B, assuming N modules associated with the target asset and times $S_{i1}$, $S_{i2}$, ..., $Si_N$ are times on the modules after the $i^{th}$ failure and after repairs have been performed. The probability that the time between the $i^{th}$ and $(i+1)^{st}$ event is less than t can be defined as:

$$F(t|s_1, s_2, \ldots, s_N) = 1 - \exp\left[\sum_{j=1}^{N}\left(\frac{s_j}{\eta_j}\right)^{\beta_j} - \sum_{j=1}^{N}\left(\frac{s_j+t}{\eta_j}\right)^{\beta_j}\right]. \quad \text{(Eq. 4)}$$

In the example of FIG. 10B, given that there is a failure at time t, the probability that module k failed is:

$$\frac{h_k(s_j+t)}{\sum_{j=1}^{N} h_j(s_j+t)}, \text{ where } h_j(s_j+t) = \left(\frac{s_j+t}{\eta_j}\right)^{\beta_j-1}\frac{\beta_j}{\eta_j}.$$

In certain examples, a conditional PDF in which module k is the $(i+1)^{st}$ failure and the time between the $i^{th}$ and $(i+1)^{st}$ failures is t given that the time on the modules after the $i^{th}$ failure is $S_{i1}$, $S_{i2}$, ..., $Si_N$ can be defined as:

$$F(t|s_1, s_2, \ldots, s_N) = \quad \text{(Eq. 5)}$$
$$1 - \exp\left[\sum_{j=1}^{N}\left(\frac{s_{ij}}{\eta_j}\right)^{\beta_j} - \sum_{j=1}^{N}\left(\frac{s_{ij}+t}{\eta_k}\right)^{\beta_j}\right]\left(\frac{s_{ik}+t}{\eta_k}\right)^{\beta_k-1}\frac{\beta_k}{\eta_k}.$$

A corresponding probability distribution function/probability density function (PDF) can be defined as:

$$F_k=(t|S_{i1}, S_{i2}, \ldots, S_{iN}) = \int_{s=0}^{t} f_k(S|S_{i1}, S_{i2}, \ldots, S_{iN})ds \quad \text{(Eq. 6)}$$

wherein $F_k$ is the PDF and $f_k$ represents individual probabilities of failure.

Figure 11:
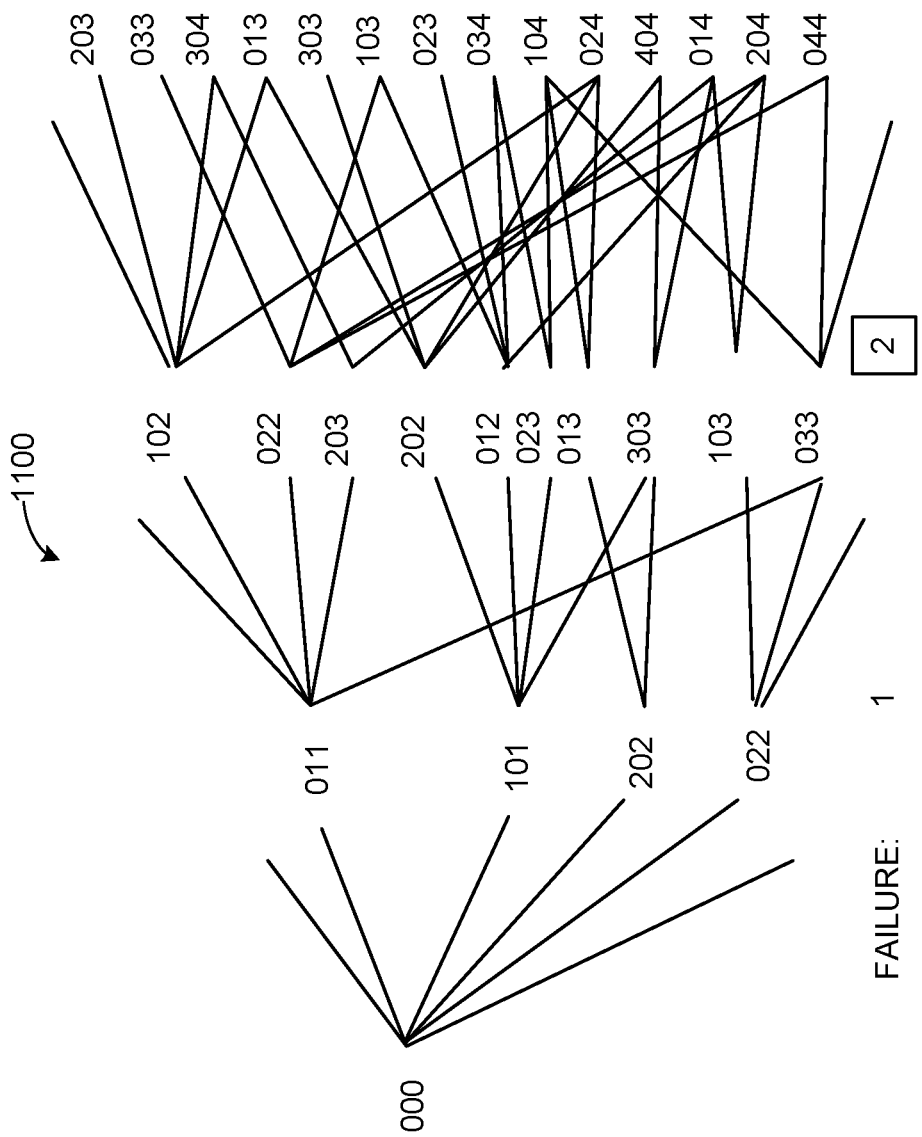
FIG. 11 illustrates an example mesh or time directed graph of state transitions and modules in a target asset.

Referring back to a mesh network or time directed graph (e.g., a time directed discrete probability graph of possible future events, etc.) such as the example of FIGS. 8-9B, a probability distribution of possible future events (e.g., errors, failures, insufficient performance, shop visit, etc.) can be represented as paths built on a finite mesh. The time directed graph has a size m (e.g., 1000 cycles, 25,000 cycles, etc.). Network state is given by time on each module. FIG. 11 illustrates an example network graph 1100 in which it is assumed that only a failing module is repaired. As shown in the example of FIG. 11, a "0" indicates which module failed. For example, 023 indicates 0 cycles on module 1, 2 m cycles on module 2, and 3 m cycles on module 3. A probability of going from 1,0,1 to 0,2,3 can be represented as:

$$\int_{m}^{2m} f_1(t|m,0,m)dt = F(wm|m,0,m) - F_1(M|m,0,m).$$

Thus, with a mesh or network size m, a probability of going from state $a_{i1}, a_{i2}, \ldots, a_{iN}$ to state $a_{i1}+b, a_{i2}+b, \ldots a_{i,k-1}+b, 0, a_{i,k+1}+b, \ldots, a_{iN}+b$ is given by:

$$\int_{m(b-1)}^{mb}(t|ma_{i1}, \ldots, ma_{iN})dt = F_k(mb|ma_{i1}, \ldots, ma_{iN}) - F_{k(m(b-1)|ma_{i1}, \ldots, ma_{iN})} \quad \text{(Eq. 7)}.$$

The righthand side of Equation 7 can be simplified as $F_k(mb) - F_k(m(b-1))$.

To determine a total probability, P, that module k will be the next failing module given a time horizon T with S hours already passed, the WSA 515 can calculate:

$$P = \sum_{j=S/m+1}^{T/m}[F_k(jm) - F_k((j-1)m)] \quad \text{(Eq. 8)}.$$

A probability that the first L failures between time 0 and time T will be due to modules $k_1, k_2, \ldots, k_L$ can be calculated by:

$$P = \sum_{j_1=1}^{T/m-(L-1)} \sum_{j_2=j_1}^{T/m-(L-2)} \cdots \sum_{j_L=j_1+j_2+\ldots+j_L-1}^{T/m} [F_{k_1}(j_1 m) - F_{k_1}((j_1-1)m)] \times [F_{k_2}(j_2 m) - F_{k_2}((j_2-1)m)] \cdots [F_{k_L}(j_L m) - F_{k_L}((j_L-1)m)] \quad \text{(Eq. 9)}.$$

Taking the limit as m approaches zero generates:

$$P = \int_{t_1=0}^{T} \int_{t_2=0}^{T-t_1} \cdots \int_{t_L=0}^{T-t_1-t_2-\ldots-t_{L-1}} F_{k_1}(t_1|0,0,\ldots,0) f_{k_2}(t_2|s_{1_1}, \ldots, s_{1N}) \cdots f_{k_L}(t_L|s_{L-1,1}, \ldots, s_{L-1,N}) dt_1 dt_2 \ldots \quad \text{(Eq. 10)},$$

where $t_1$ is time from $SV_{i-i}$ to $SV_i$.

Thus, the WSA 515 generates an "optimal" and/or otherwise desirable workscope for execution with respect to a target asset such as an engine, engine module/subsystem (e.g., high pressure compressor, fan/low pressure compressor, combustor, high pressure turbine, low pressure turbine, accessory drive, etc.), etc., using the workscope model analyzer 710 in conjunction with the asset state analyzer 705 and workscope value evaluator 715. The WSA 515 provides expected revenue, expected cost, expected operating margin, expected LLP financials, etc., via the workscope value evaluator 715. Model analysis and simulation allow the WSA 515 to narrow a set of available workscopes for a target asset to a selected optimal workscope for execution via the workscope selector 520. Using model analysis, simulation, and dynamic programming via a state-based mesh model, the WSA 515 generates and evaluates a probability of future shop visits for the asset, likely drivers of future shop visits, and expected time-on-wing until future shop visits, for example.

A decision made by the workscope model analyzer 710 triggers an action made at a current stage to effect asset operation as well as overall cost/profit and/or other benefit, value, etc. Decisions are associated with a value (e.g., cost/benefit, etc.), as well as a chosen workscope, for example. The WSA 515 provides cost/benefit value information along with workscope data to the workscope selector 520 to produce the selected optimal workscope as output 355. Such value can be bounded and/or otherwise affected by restrictions and/or constraints such as time horizon, rates, limits on time between asset component maintenance, and other soft and/or hard constraints specified by a contract, for example. The selected workscope triggers an assignment of maintenance personnel, a service facility, spare parts, tools, etc., to repair and/or replace the asset according to the workscope based on a removal schedule, for example.

In some examples, the outputs 355 include a removal schedule of one or more assets including corresponding removal schedule information (e.g., maintenance logistic information, service logistic information, etc.). For example, the outputs 355 can include a removal schedule of the engine 102 including a maintenance facility in which the engine 102 can be serviced and a timeline in which the engine 102 can be removed, serviced, and re-deployed. In certain examples, availability of spare assets (e.g., spare engines, etc.) such as 5% of fleet size, 10% of fleet size, 15% of fleet size, etc., factors into the output 355 such that the WSA 515 helps to predict and control a number of spare assets and/or other parts to be available for a duration of maintenance of the target asset in the shop (e.g., a spare engine to replace an engine being taken off wing and brought into the shop for repair, etc.).

While an example implementation of the task optimizer 310 of FIG. 3 is illustrated in FIGS. 4-7, one or more of the elements, processes and/or devices illustrated in FIGS. 4-7 can be combined, divided, re-arranged, omitted, eliminated and/or implemented in any other way. Further, the example workscope drivers 505, the example workscope mapper 510, the example workscope strategy analyzer 515, the example workscope selector 520, and/or, more generally, the example task optimizer 310 of FIG. 3 can be implemented by hardware, software, firmware and/or any combination of hardware, software and/or firmware. Thus, for example, any of the example workscope drivers 505, the example workscope mapper 510, the example workscope strategy analyzer 515, the example workscope selector 520, and/or, more generally, the example task optimizer 310 can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example workscope drivers 505, the example workscope mapper 510, the example workscope strategy analyzer 515, the example workscope selector 520, and/or, more generally, the example task optimizer 310 is/are hereby expressly defined to include a non-transitory computer readable storage device or storage disk such as a memory, a digital versatile disk (DVD), a compact disk (CD), a Blu-ray disk, etc. including the software and/or firmware. Further still, the example task optimizer 310 of FIG. 3 may include one or more elements, processes and/or devices in addition to, or instead of, those illustrated in FIGS. 4-7, and/or may include more than one of any or all of the illustrated elements, processes and devices.

Figure 12:
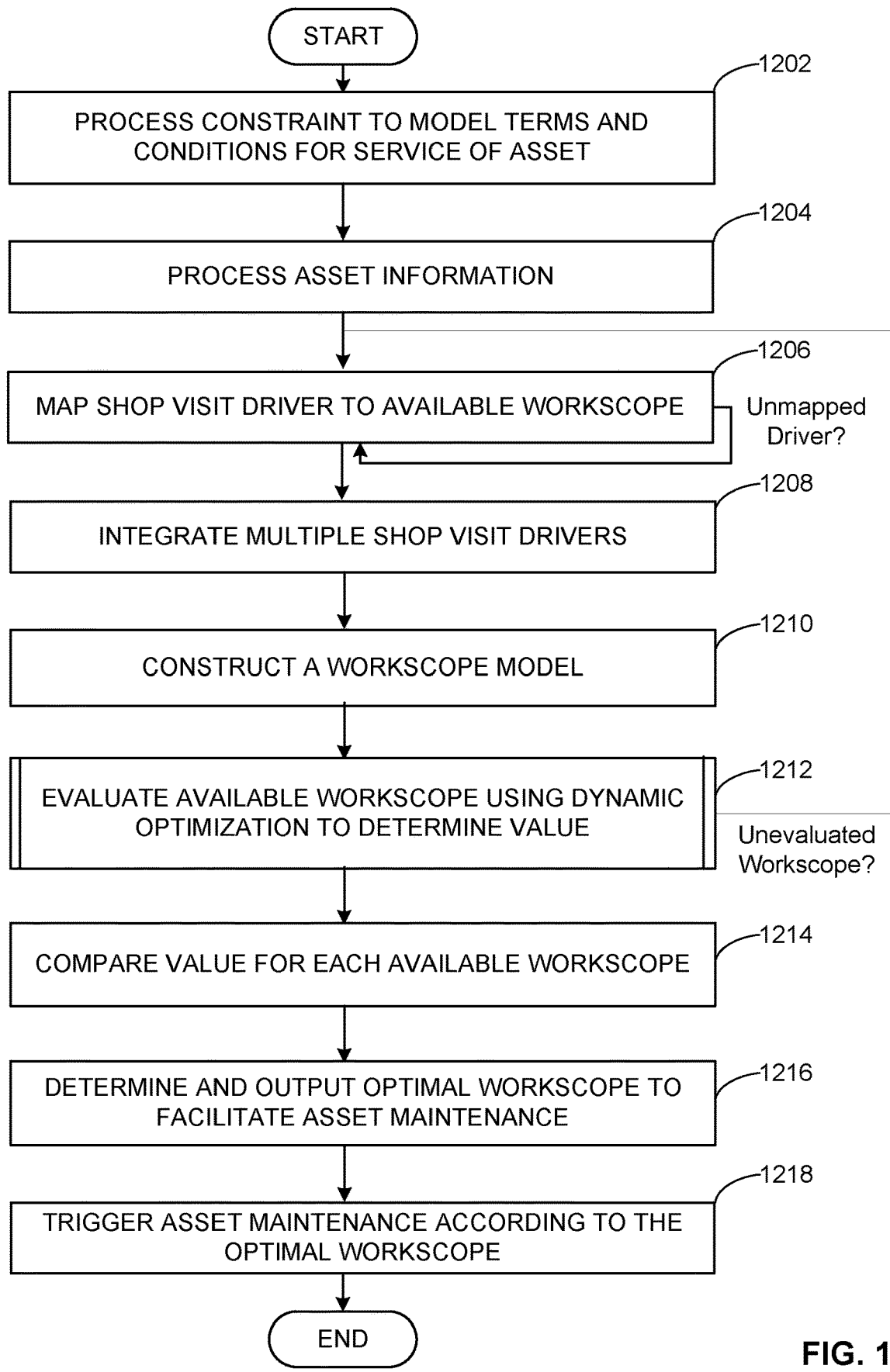
FIGS. 12 and 14 are flowcharts representative of an example method that can be executed by the example asset workscope generation system of FIGS. 3-7 to implement the examples disclosed herein.
Figure 14:
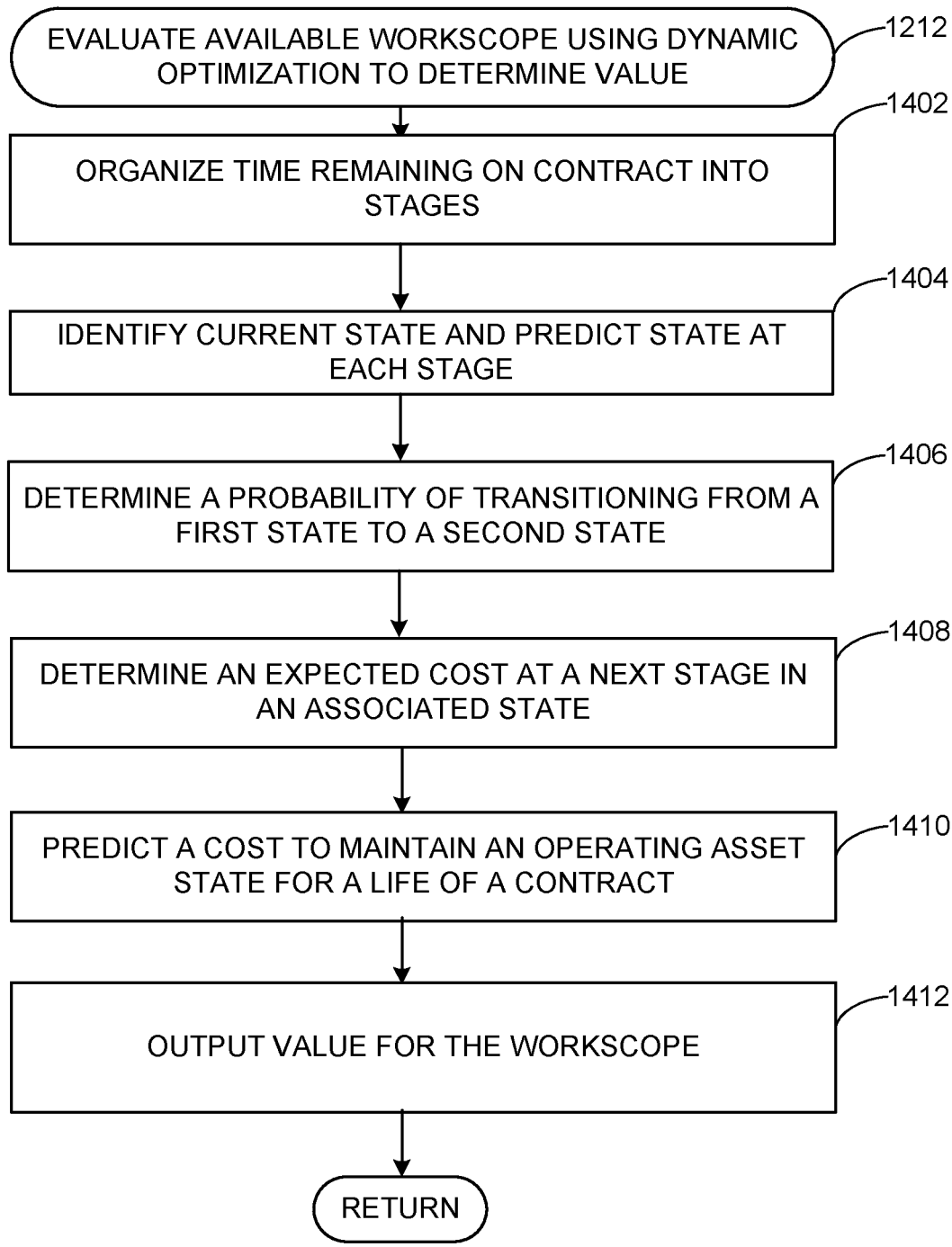

Flowcharts representative of example machine readable instructions for implementing the AWGS 220 and/or its task optimizer 310 of FIGS. 2-7 are shown in FIGS. 12 and 14. In these examples, the machine readable instructions comprise a program for execution by a processor such as a processor 1612 shown in the example processor platform 1600 discussed below in connection with FIG. 16. The program may be embodied in software stored on a non-transitory computer readable storage medium such as a CD-ROM, a floppy disk, a hard drive, a DVD, a Blu-ray disk, or a memory associated with the processor 1612, but the entire program and/or parts thereof could alternatively be executed by a device other than the processor 1612 and/or embodied in firmware or dedicated hardware. Further, although the example program is described with reference to the flowcharts illustrated in FIGS. 12 and 14, many other methods of implementing the example AWGS 220 and/or its task optimizer 310 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIGS. 12 and 14 can be implemented using coded instructions (e.g., computer and/or machine readable instructions) stored on a non-transitory computer and/or machine readable medium such as a hard disk drive, a flash memory, a read-only memory, a CD, a DVD, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open ended in the same manner as the term "comprising" and "including" are open ended.

FIG. 12 is a flowchart representative of an example method that can be performed by the example task optimizer 310 of FIGS. 3-7 to evaluate available workscopes and determine an optimal or otherwise improved workscope for maintenance of a target asset. The example method begins at block 1202 at which a contract for servicing of a target asset (and/or other set of restrictions and/or constraints) is processed by the task optimizer 310 to identify terms and conditions such as maintenance requirements, contract end date, and end asset state, etc. For example, a service contract, such as a customized service agreement (CSA), etc., can be parsed by the workscope mapper 510 and workscope drivers 505 to organize (e.g., model, etc.) the contract and/or other set of requirements and constraints in a data structure according to terms and conditions including asset and/or asset module(s) covered, duration, milestones, deliverables, etc. The data structure enables elements of the requirements and/or constraints to be modeled and compared (e.g., to each other, to components in other contracts, to status and/or feedback data regarding the target asset/asset module, etc.). The parsing, organization, and storage of contract elements in the data structure allows a workscope for an asset to be automatically tailored to the contract and/or other requirement(s)/constraint(s) for that asset, for example. The data structure can be stored as a model 335, in the database 345, as a workscope driver 505 (e.g., contract requirements 620), etc.

At block 1204, asset information is processed by the task optimizer 310. For example, target asset status, shop visit driver(s), LLP status, service bulletin state, etc., are processed. For example, current asset health from the asset health calculator 300, model input 335, database 345 information, workscope driver(s) 505, can be processed to evaluate current asset health, asset durability, life-limited part status, outstanding SB, etc., as workscope drivers 505. Asset failure rate, model/type/part number, status/health, etc., can be processed for use in evaluating workscope (e.g., according to Equations 1-10), building a digital model or twin of the asset/asset module, etc. By processing the target asset and/or a subsystem or module of the target asset, the task optimizer 310 can understand the characteristics, behavior, condition/status, and likely failure of the asset/asset module, for example.

At block 1206, each shop visit driver (e.g., failure mode distributions, etc.) is mapped to a potential workscope for an associated part of the target asset. For example, a target asset module (e.g., an engine module such as a fan, booster, compressor, etc.) is analyzed by the workscope mapper 510 with respect to shop visit driver(s) 505 such as failure mode/engine health assessment 605, durability model 610, engine LLP status 615, contract requirements and/or other restriction(s)/constraint(s) 620, SB requirements 625, etc., that are and/or can be driving a shop visit for the asset module. The driver(s) 505 are used by the workscope mapper 510 to craft an appropriate (e.g., minimum, ideal, improved, beneficial, cost-effective, etc.) workscope to address the health of the target asset module to restore a level of capability and/or performance for the asset module as indicated by the contract requirements 620, SB requirements 625, etc. Each shop visit/workscope driver 505 is modeled and an associated probability of success, time to next failure, performance, etc., is evaluated over time at one or more decision points during the life of the asset/period of the contract for a lowest cost and/or best value (e.g., cost versus benefit) maintenance solution. In certain examples, block 1206 repeats until drivers have been mapped to the available workscope.

At block 1208, multiple shop visit drivers are integrated, each shop visit driver represented by a logic or analytic to drive workscoping decisions. Thus, block 1206 can be repeated by the workscope mapper 510 for a plurality of drivers 505 to generate a plurality of workscope models or other logical representations. For example, for each mapped workscope driver 505, at least one of a deterministic time limit or a probability of repair/replacement is associated with the driver 505. A workscope associated with the combination of mapped drivers 505 is to restore, partially or fully, a time count for a set of parts/modules involved in the target asset for which a workscope is sought. For each workscope, a probability distribution of when the next shop visit will/is likely to occur can be calculated for cost/benefit (e.g., value) trade-off analysis. An overall deterministic time limit can be calculated by the workscope mapper 510 from the plurality of individual workscope driver time limit and probability distributions, for example.

At block 1210, a workscoping model is constructed with associated price, cost and billing structure. For example, a model, such as a digital twin of the asset and associated workscope, a logical representation of tasks, materials, timing, cost, benefit, contract terms, etc., forming the workscope, etc., is generated by the workscope mapper to represent and facilitate processing of the workscope with respect to the asset/asset module. Asset (and/or asset module), task(s), failure mode distribution, price, cost, and billing structure (e.g., per contract terms, etc.), etc., can be represented for use, processing, reporting, etc., via the workscope model.

At block 1212, the available workscope is evaluated using dynamic optimization to determine a cost and benefit associated with the workscope. For example, an impact (e.g., a financial impact, TOW impact, contract impact, performance impact, etc.) is computed over a life of the contract for the target asset assuming a specific workscope combining probability failure modes, discrete events, and contract specifications. For example, mathematical processing (e.g., computing a probability distribution of expected maintenance activities within a selected workscope such as in Equations 4-10, etc.) by the WSA 515 computes a life of contract (LOC) financial impact for a workscope. Contract details including payment structure, removal scheduling requirements, life limited parts (LLP), financial considerations (e.g., resale value of used parts, spare part availability, etc.), workscope cost, interdependency of workscope for asset modules, probability of engine removal due to different workscope drivers and deterministic drivers, other restrictions(s) and/or constraint(s), etc., are provided as input to analyze a probability of a next state at each decision point in the LOC until a final outcome (see, e.g., the example network 800 and associated probabilities 808 from a current decision point 804 to final outcome(s) 810 at the end of the LOC as shown in the example of FIG. 8). For each potential workscope, an expected cost, price, and operating margin are computed over the LOC by the WSA 515. Thus, the expected cost to maintain the target asset over the LOC can be determined for an available workscope and used to evaluate the associated workscope in comparison to other available workscopes.

Figure 13:
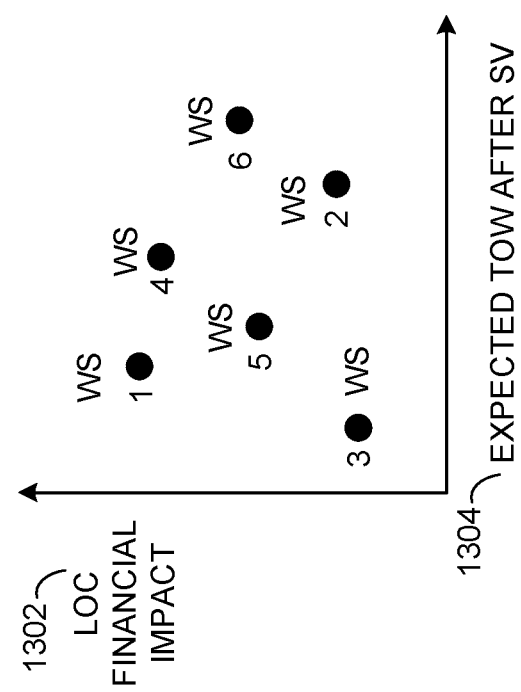
FIG. 13 is an example graph of expected time-on-wing after shop visit versus financial impact for the life of a contract for a plurality of workscopes.

FIG. 13 illustrates an example diagram comparing LOC financial impact 1302 and/or other desired objective function to expected TOW after shop visit 1304 for workscope 1-workscope 6 (WS1-WS6). Thus, different workscopes have a different financial impact over the life of the contract (e.g., greater or less cost than other workscope alternatives) as well as more or less TOW following the shop visit when compared to other workscope alternatives. Such financial impact enables a tradeoff analysis for engine removal and optimal and/or otherwise improved workscope selection, for example.

Thus, at block 1212, failure mode probabilities and financial impact are combined with workscoping options using dynamic optimization propagated to an end of the contract. A likelihood or probability of failure, a financial impact of the failure, and a cost for shop visit are combined with available workscope options by the WSA 515 using dynamic programming optimization to extrapolate the cost/benefit through the end of the contract for service of the asset.

For example, by evaluating a system/asset state for each of a plurality of decision points representing workscope options at a given stage in the life of an asset/contract, a cost/benefit analysis can be automatically generated by the WSA 515 to select an available workscope that maximizes and/or otherwise increases benefit/profit (e.g., ease of repair, cost-effectiveness, timeliness, efficient, capability, etc.) with respect to cost at a given point in the LOC for the asset/asset module. In certain examples, the cost/benefit (e.g., value) analysis is extrapolated from the current decision point to subsequent decision points in the future leading to the end of the contract and/or other constraint/restriction. As shown in the example network 800 of FIG. 8, from a current decision point 804, a plurality of next decision points 806 have a certain probability 808 of occurring. As shown in FIGS. 9A-9B, a lowest cost path between desirable outcomes along the way from start 902 to end 904 of contract/usable life of the asset can represent a desirable workscope for selection and implementation with respect to the asset/asset module, for example. As described above, a stochastic and/or deterministic dynamic programming optimization can be executed by the WSA 515 with respect to available workscopes for the target asset and its contract and/or other restriction/constraint/requirement to determine an "optimal" workscope give asset (e.g., engine, etc.) age, time on module, shop visit driver(s), etc.

For example, assuming an LOC for the asset can be divided into M stages, the asset is in stage k if the asset is currently in the shop and the probability of reaching the limit in M-k or fewer additional shop visits is greater than a level of certainty P (e.g., P=0.80, 0.90, 0.99, etc.). The asset has a state at each of the M stages up to end-of-life/end-of-contract for the asset. As shown in the example of FIGS. 10A-10B, asset state can be represented as events 1002, 1004 and/or associated workscopes 1006, 1008 with associated failures 1010, 1012 based on state of the asset when it leaves the shop (e.g., time on each module, etc.) and how the asset is operated (e.g., captured in Weibull parameters, etc.), where time follows a specific probability distribution/density function as specified by Equations 1-10. Probability can then be used to determine whether an asset and/or asset module will be the next module to failure and, therefore, should be included the workscope. The probability of stage and state for an available workscope can be compared to probability associated with another available workscope to evaluate and select an "optimal" workscope for the target asset to maximize and/or otherwise improve cost/benefit for the contract associated with servicing of the target asset.

At block 1214, the cost versus benefit and/or other value generated through dynamic optimization processing of the available workscopes performed at block 1212 is compared for each available workscope. For example, a cost (e.g., determined according to Equations 1-3, etc.) calculated at block 1212 for each available workscope can be compared to evaluate which available workscope has the lowest associated cost. In certain examples, a quantification of the benefit (e.g., parts repaired, parts replaced, time-on-wing, incentives gained, etc.) can be applied to balance the cost of the respective workscope such that the comparison at block 1214 is an evaluation by the WSA 515 of the cost/benefit for each available workscope to determine which available workscope provides the best benefit at the lowest cost.

At block 1216, an optimal and/or otherwise improved workscope is determined based on the dynamic optimization processing of the available workscopes, and the optimal workscope is output to facilitate asset maintenance (e.g., repair, replacement, etc.). For example, based on the stochastic and/or deterministic dynamic programming optimization applied at block 1212 and the comparison evaluated by the WSA 515 at block 1214, the available workscope that satisfies likely probabilities of asset module/asset failure while reducing/minimizing cost can be selected as the "optimal" workscope, for example. The optimal and/or otherwise improved workscope is determined by the WSA 515 and output via the workscope selector 520 as output 355. Thus, based on the analysis of the WSA 515, the workscope selector 520 selects optimal workscope(s) for a current shop visit that satisfies contract requirements and minimizes expected costs and/or increases time on wing through the end of the contract for the asset in question.

At block 1218, asset maintenance is triggered according to the optimal workscope. For example, the determined workscope (e.g., including tasks to be executed, materials to be used, asset(s)/asset module(s) to be taken offline/off-wing, spare/leased asset(s) to replace part(s) in shop, etc.) can be provided to an asset maintenance system, scheduling system, etc., to take affected asset(s) off-wing and/or otherwise off-line, arrange for temporary replacement, and trigger repair/replacement of the affected asset/asset module(s).

FIG. 14 is a flowchart representative of an example implementation of block 1212 of the example of FIG. 12 to evaluate an available workscope using dynamic optimization to determine value. For example, failure mode probabilities and financial impact can be combined with an available workscope option using dynamic optimization propagated to an end of a contract for the target asset. At block 1402, time remaining on the contract for service of the target asset is organized into stages. For example, starting with a current point in time, the remaining LOC is divided into stages, each stage associated with one or more probable/possible states. Each stage represents a decision point with respect to the target asset (e.g., engine, engine module, etc.). The decision point indicates an action made at the respective stage to affect the asset and overall cost/profit with respect to the contract (e.g., associated workscope, etc.).

At block 1404, a current state is identified, and a state to be associated with each stage is predicted. An associated state indicates a condition of the asset at the respective stage (e.g., time-on-engine, time-on-modules, shop visit driver, etc.). A prediction of a next state at a next stage can be calculated as described above with respect to Equations 4-10. For example, asset states can be characterized as events 1002, 1004, such as failures 1010, 1012, associated with workscopes 1006, 1008.

At block 1406, a probability of transitioning from a first state to a second state is determined. For example, a probability distribution can be generated based on a transition from a current state to a next state for an asset module at a predicted time (see, e.g., Equations 4-10 and FIGS. 8-11, etc.). For example, a probability distribution from on-wing to off-wing (or vice-versa) for the engine can be determined.

At block 1408, an expected cost at a next stage in an associated state is determined. For example, a cost associated with the state of the asset at the next stage and tasks involved to maintain the asset based on the asset state is calculated based on contract terms, cost of parts and labor, spare engine/leased engine cost, time off wing, etc.

At block 1410, a cost to maintain the operating state for the life of the contract is predicted. For example, using the continuous stochastic model of Equation 3, a distribution of possible outcomes is dynamically evaluated to compute a minimum expected cost when N stages remain in the LOC and the LOC for the asset is at stage i. By integrating the probability density function and associating with workscope cost, the minimum expected cost for an available workscope over the remaining LOC can be determined (see, e.g., Equations 1-3). Thus, each workscope driver is a time limit and/or probability distribution, and Equations 1-3 can be used to compute the financial impact over the life of the contract of a given asset assuming a specific workscope combining probability failure modes, discrete events and contract specifications. At block 1412, a value is output for the particular workscope.

As recited in the example method 1200, for each available workscope, a corresponding workscope model is evaluated based on a mathematical method involving contract details including payment structure, removal scheduling requirements, life limited parts, financial considerations as resale value of used parts, workscope cost, interdependency of workscope for modules, probability of engine removals due to different workscope drivers and deterministic drivers to compute the expected cost, price and operating margin over the life of the contract and/or other set of restrictions and/or constraints and enable tradeoff analysis for engine removal and optimal workscope selection. Thus, a likelihood or probability of failure, a financial impact of the failure, and a cost for shop visit are combined with available workscope options by the WSA 515 using dynamic programming optimization to extrapolate the cost/benefit (e.g., value) through the end of the contract for service of the asset.

FIG. 15 depicts example source code 1500 representative of example computer readable instructions that can be executed to implement the example task optimizer 310 including the example WSA 515 that can be used to implement the examples disclosed herein. For example, the source code 1500 can be used to implement the method of FIGS. 12 and 14. As shown in the example of FIG. 15, the source code 1500 represents instructions to evaluate each remaining stage for each available workscope to evaluate a cost associated with the respective workscope to maintain the asset through the LOC. For each stage from the end stage to the current stage, a workscope decision cost plus a cost associated with a probability of changing states is determined such that associated costs can be compared for each stage to identify a stage associated with a best value (e.g., a minimum cost, most benefit, etc.).

Figure 16:
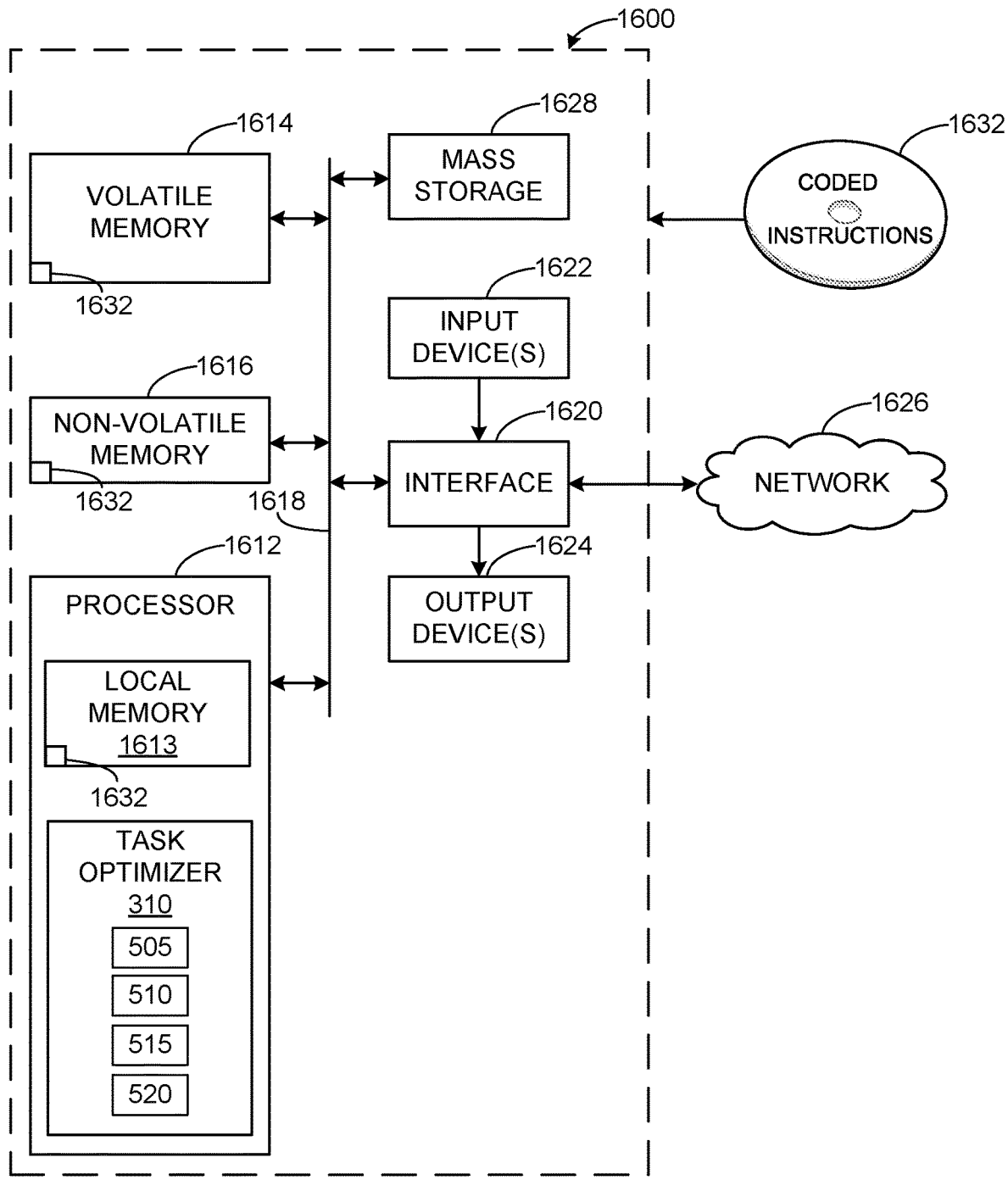
FIG. 16 is a block diagram of an example processing platform structured to execute machine-readable instructions to implement the methods of FIGS. 12 and 14 and/or the example asset workscope generation system of FIGS. 3-7.

FIG. 16 is a block diagram of an example processor platform 1600 capable of executing the instructions of FIGS. 12, 14 and 15 to implement the task optimizer 310 and/or the AWGS 220 of FIGS. 2-7. The processor platform 1600 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1600 of the illustrated example includes a processor 1612. The processor 1612 of the illustrated example is hardware. For example, the processor 1612 can be implemented by one or more integrated circuits, logic circuits, microprocessors or controllers from any desired family or manufacturer. The hardware processor may be a semiconductor based (e.g., silicon based) device. In this example, the processor 1612 implements the example workscope drivers 505, the example workscope mapper 510, the example workscope strategy analyzer 515, and the example workscope selector 520 of the example task optimizer 310.

The processor 1612 of the illustrated example includes a local memory 1613 (e.g., a cache). The processor 1612 of the illustrated example is in communication with a main memory including a volatile memory 1614 and a non-volatile memory 1616 via a bus 1618. The volatile memory 1614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1616 may be implemented by flash memory and/or any other desired type of memory device. Access to the main memory 1614, 1616 is controlled by a memory controller.

The processor platform 1600 of the illustrated example also includes an interface circuit 1620. The interface circuit 1620 may be implemented by any type of interface standard, such as an Ethernet interface, a universal serial bus (USB), and/or a peripheral component interconnect (PCI) express interface.

In the illustrated example, one or more input devices 1622 are connected to the interface circuit 1620. The input device(s) 1622 permit(s) a user to enter data and/or commands into the processor 1612. The input device(s) can be implemented by, for example, an audio sensor, a microphone, a camera (still or video), a keyboard, a button, a mouse, a touchscreen, a track-pad, a trackball, an isopoint device, and/or a voice recognition system.

One or more output devices 1624 are also connected to the interface circuit 1620 of the illustrated example. The output devices 1624 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1620 of the illustrated example, thus, typically includes a graphics driver card, a graphics driver chip and/or a graphics driver processor.

The interface circuit 1620 of the illustrated example also includes a communication device such as a transmitter, a receiver, a transceiver, a modem and/or network interface card to facilitate exchange of data with external machines (e.g., computing devices of any kind) via a network 1626 (e.g., an Ethernet connection, a digital subscriber line (DSL), a telephone line, coaxial cable, a cellular telephone system, etc.).

The processor platform 1600 of the illustrated example also includes one or more mass storage devices 1628 for storing software and/or data. Examples of such mass storage devices 1628 include floppy disk drives, hard drive disks, compact disk drives, Blu-ray disk drives, redundant array of independent disks (RAID) systems, and DVD drives.

The coded instructions 1632 of FIGS. 12, 14, and 15 can be stored in the mass storage device 1628, in the volatile memory 1614, in the non-volatile memory 1616, and/or on a removable non-transitory computer readable storage medium such as a CD or DVD.

From the foregoing, it will be appreciated that example methods, apparatus and articles of manufacture have been disclosed that generate, evaluate, and select among a plurality of available workscopes for maintenance of a target asset, such as a turbine engine, engine module, diesel engine, wind turbine, other asset requiring maintenance, etc. The above-disclosed task optimizer apparatus can optimize and/or otherwise improve generation and selection of a desired workscope based on a plurality of factors including expected cost, operating margin over the life of an associated contract, time in shop, time before next failure, etc. The task optimizer apparatus performs a tradeoff analysis based on these factors, and facilitates maintenance of the target asset (e.g., removal of the asset, shop visit for repair/replacement, temporary asset substitution while in shop, etc.). Certain examples leverage contract information such as payment structure, asset removal scheduling requirements, life limited parts, financial considerations such as resale value of used parts and operating margin, workscope cost, asset module workscope interdependency, probability of asset removal due to different workscope drivers and deterministic drivers, etc., to determine an expected cost and benefit for each available workscope to select a best or "optimal" workscope among the available workscope alternatives. Workscope determination is automated and customized to the contract and target asset, for example. Both deterministic and probabilistic events are evaluated to provide a more complete picture or model of the asset and its operating environment.

When faced with millions of possibilities, the task optimizer and its workscope strategy analyzer determine a subset of available workscopes and, for each available workscope in the subset, the analyzer predicts, for the future, when a next shop visit is likely to be warranted. The workscope strategy analyzer models based on available workscopes and probabilities to predict what types of workscopes are likely to be available at future points in time during the life of the associated contract based on stage and state, and the analyzer evaluates a plurality of decision points or stages from a starting point until an end of the life of the contract is reached. The example workscope strategy analyzer determines an optimal path among the predicted path options to reach the end of the life of the contract and computes the total cost for the selected workscope path. Total cost and expected payment by customer can be evaluated with optimal workscope path to select a workscope from the available workscope alternatives. The task optimizer then triggers and facilitates maintenance of the target asset based on the determined "optimal" or otherwise improved workscope and its associated tasks, resources, timing, etc. For example, rather than a Monte Carlo simulation (e.g., involving 1000 iterations using random numbers starting with a seeded starting point, etc.) and/or other estimate, certain examples disclosed herein provide an exact solution for workscope determination.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
a task generator configured to generate a set of tasks to be performed on a target asset based on workscope drivers including asset information of the target asset and constraint information associated with contract requirements for the target asset;
a workscope mapper configured to: (i) receive the workscope drivers and process the asset information and the constraint information to generate a model of a target asset and a model of a constraint associated with the target asset, map the workscope drivers to a plurality of workscopes using the target asset model and the associated constraint model, each of the plurality of workscopes modeling maintenance of the target asset including the tasks and resources associated with the maintenance of the target asset, and (iii) dynamically adjust mapping of the workscope drivers based on changes to the asset information according to feedback received from the target asset;
a workscope strategy analyzer to evaluate each of the plurality of workscopes using dynamic optimization to determine a maintenance value to the target asset associated with each workscope based on a stage in a remaining life of the constraint at which the evaluation is executed and a state of the target asset, wherein the dynamic optimization is performed to predict the maintenance value based on a probability of a future change in state and an associated workscope value including cost corresponding to each workscope of the plurality of workscopes until an end of the remaining life of the constraint, and the maintenance value as predicted by the dynamic optimization is a minimum sum of the associated workscope values of the plurality of workscopes until the end of the remaining life of the constraint, wherein the probability of a future change in state is determined by forming a time directed discrete probability graph of possible stages and associated states for the remaining life of the constraint; and
a workscope selector to select a workscope from the plurality of workscopes based on the evaluation of the plurality of workscopes by the workscope strategy analyzer including comparison of the maintenance value associated with each workscope of the plurality of workscopes, the workscope selector to trigger maintenance with respect to the target asset according to the selected workscope.

2. The apparatus of claim 1, wherein the target asset includes a turbine engine.

3. The apparatus of claim 1, wherein the probability is associated with a path between possible stages and associated states for the remaining life of the constraint.

4. The apparatus of claim 1, wherein the selected workscope includes a system-level workscope formed as an aggregate of workscope for each of a plurality of modules of the target asset.

5. The apparatus of claim 1, wherein the selected workscope represents a minimum set of tasks and resources to restore a level of performance in the target asset as prescribed in the constraint.

6. The apparatus of claim 1, wherein each stage in the remaining life of the constraint is associated with a probable failure.

7. The apparatus of claim 1, wherein each shop visit driver is represented by at least one of a deterministic time limit for maintenance of the target asset or a probabilistic distribution of a chance for failure of the target asset.

8. The apparatus of claim 1, wherein the dynamic optimization of the workscope strategy analyzer includes calculating, for each of the plurality of workscopes, a probability distribution of a next shop visit and comparing the probability to an associated value.

9. The apparatus of claim 1, wherein the dynamic optimization determines the maintenance value for a respective workscope according to $$V_N(i) = \min_{a \in W}\left[C(i, a) + \int f(a)V_{N-1}(j)\right],$$

for $0 < N < M$, wherein:
i represents a first state;
j represents a second state;
a represents a workscope decision;
W represents the plurality of workscopes;
M represents a number of stages within the constraint;
N represents a number of stages in the remaining life of the constraint;
C(i,a) represents a current cost of making decision a in state i;
f(a) represents a probability density function for going from state i to state j based on decision a; and
$V_N(i)$ represents a minimum expected cost associated with the respective workscope at state i with N stages in the remaining life of the constraint.

10. A non-transitory computer readable storage medium comprising instructions which when executed, cause a machine to implement at least:
- generating, via a task generator, a set of tasks to be performed on a target asset based on workscope drivers including asset information of the target asset and constraint information associated with contract requirements for the target asset;
- receiving, via a workscope mapper workscope drivers and processing the asset information and the constraint information to generate a model of a target asset and a model of a constraint associated with the target asset, mapping, via the workscope mapper the workscope drivers to a plurality of workscopes using the target asset model and the associated constraint model, each of the plurality of workscopes modeling maintenance of the target asset including the tasks and resources associated with the maintenance of the target asset and dynamically adjust mapping of the workscope drivers based on changes to the asset information according to feedback received from the target asset;
- evaluating, via a workscope strategy analyzer each of the plurality of workscopes using dynamic optimization to determine a maintenance value and a benefit to the target asset associated with each workscope based on a stage in a remaining life of the constraint at which the evaluation is executed and a state of the target asset, wherein the dynamic optimization is performed to predict the maintenance value based on a probability of a future change in state and an associated workscope value including cost corresponding to each workscope of the plurality of workscopes until an end of the remaining life of the constraint, and the maintenance value as predicted by the dynamic optimization is a minimum sum of the associated workscope values of the plurality of workscopes until the end of the remaining life of the constraint, wherein the probability of a future change in state is determined by forming a time directed discrete probability graph of possible stages and associated states for the remaining life of the constraint; and
- selecting, via a workscope selector a workscope from the plurality or workscopes based on the evaluation of the plurality of workscopes by the workscope strategy analyzer including comparison of the maintenance value associated with each workscope of the plurality of workscopes, the workscope selector to trigger maintenance with respect to the target asset according to the selected workscope.

11. The non-transitory computer readable storage medium of claim 10, wherein the selected workscope includes a system-level workscope formed as an aggregate of workscope for each of a plurality of modules of the target asset, the selected workscope representing a minimum set of tasks and resources to restore a level of performance in the target asset as prescribed in the constraint.

12. The non-transitory computer readable storage medium of claim 10, wherein each stage in the remaining life of the constraint is associated with a probable failure.

13. The non-transitory computer readable storage medium of claim 10, wherein each workscope driver is represented by at least one of a deterministic time limit for maintenance of the target asset or a probabilistic distribution of a chance for failure of the target asset.

14. The non-transitory computer readable storage medium of claim 10, wherein the dynamic optimization of the workscope strategy analyzer includes calculating, for each of the plurality of workscopes, a probability distribution of a next shop visit and comparing the probability to an associated value.

15. A computer-implemented method comprising:
- generating, via a task generator, a set of tasks to be performed on a target asset based on workscope drivers including asset information of the target asset and constraint information associated with contract requirements for the target asset;
- receiving, via a workscope mapper workscope drivers and processing the asset information and the constraint information to generate a model of a target asset and a model of a constraint associated with the target asset;
- mapping, via the workscope mapper, the workscope drivers to a plurality of workscopes using the target asset model and the associated constraint model, each of the plurality of workscopes modeling maintenance of the target asset including the tasks and resources associated with the maintenance of the target asset and dynamically adjust mapping of the workscope drivers based on changes to the asset information according to feedback received from the target asset;
- evaluating, via a workscope strategy analyzer, each of the plurality of workscopes using dynamic optimization to determine a maintenance value and a benefit to the target asset associated with each workscope based on a stage in a remaining life of the constraint at which the evaluation is executed and a state of the target asset, wherein the dynamic optimization is performed to predict the maintenance value based on a probability of a future change in state and an associated workscope value including cost corresponding to each workscope of the plurality of workscopes until an end of the remaining life of the constraint, the maintenance value as predicted by the dynamic optimization is a minimum sum of the associated workscope values of the plurality of workscopes until the end of the remaining life of the constraint, wherein the probability of a future change in state is determined by forming a time directed discrete probability graph of possible stages and associated states for the remaining life of the constraint; and
- selecting, via a workscope selector, a workscope from the plurality of workscopes based on the evaluation of the plurality of workscopes by the workscope strategy analyzer including comparison of the maintenance value associated with each workscope of the plurality of workscopes; and
- triggering, based on the selected workscope and using the workscope selector, maintenance with respect to the target asset according to the selected workscope.

16. The method of claim 15, wherein the selected workscope includes a system-level workscope formed as an aggregate of workscope for each of a plurality of modules of the target asset, the selected workscope representing a minimum set of tasks and resources to restore a level of performance in the target asset as prescribed in the constraint.

17. The method of claim 15, wherein each stage in the remaining life of the constraint is associated with a probable failure.

18. The method of claim 15, wherein each shop visit driver is represented by at least one of a deterministic time limit for maintenance of the target asset or a probabilistic distribution of a chance for failure of the target asset.

19. The method of claim 15, wherein the dynamic optimization of the workscope strategy analyzer includes calculating, for each of the plurality of workscopes, a probability distribution of a next shop visit and comparing the probability to an associated value.

\* \* \* \* \*